US009255928B2

(12) United States Patent
Reichardt et al.

(10) Patent No.: US 9,255,928 B2
(45) Date of Patent: Feb. 9, 2016

(54) METHOD FOR THE CHARACTERIZATION OF INTERMOLECULAR INTERACTIONS

(75) Inventors: Niels-Christian Reichardt, San Sebastián (ES); Juan Etxebarria Ruiz, San Sebastián (ES)

(73) Assignee: Centro de Investigación Cooperativa en Biomateriales (CIC biomaGUNE), San Sebastián (ES)

( * ) Notice: Subject to any disclaimer, the term of this patent is extended or adjusted under 35 U.S.C. 154(b) by 0 days.

(21) Appl. No.: 13/806,636

(22) PCT Filed: Jun. 22, 2011

(86) PCT No.: PCT/EP2011/060431
§ 371 (c)(1),
(2), (4) Date: Jan. 29, 2013

(87) PCT Pub. No.: WO2011/161150
PCT Pub. Date: Dec. 29, 2011

(65) Prior Publication Data
US 2013/0123137 A1 May 16, 2013

(30) Foreign Application Priority Data
Jun. 22, 2010 (EP) .................................... 10382176

(51) Int. Cl.
G01N 33/68 (2006.01)
G01N 33/50 (2006.01)

(52) U.S. Cl.
CPC ............ *G01N 33/68* (2013.01); *G01N 33/5008* (2013.01); *G01N 33/6842* (2013.01); *G01N 33/6845* (2013.01)

(58) Field of Classification Search
CPC ................................ G01N 33/68; C40B 40/12
USPC ........................................................ 506/9, 19
See application file for complete search history.

(56) References Cited

U.S. PATENT DOCUMENTS

| 2003/0153013 | A1  |   | 8/2003 | Huang          |         |
|--------------|-----|---|--------|----------------|---------|
| 2009/0215073 | A1  | * | 8/2009 | Emmert-Buck et al. | 435/7.1 |
| 2010/0203533 | A1  | * | 8/2010 | Desai et al.   | 435/6   |

FOREIGN PATENT DOCUMENTS

| WO | WO-02/48674    | A2 |   | 6/2002  |
|----|----------------|----|---|---------|
| WO | WO 0248674     | A2 | * | 6/2002  |
| WO | WO-02/083918   | A2 |   | 10/2002 |
| WO | WO-2004/048928 | A2 |   | 6/2004  |
| WO | WO-2006/113245 | A2 |   | 10/2006 |
| WO | WO 2007082057  | A2 | * | 7/2007  |

OTHER PUBLICATIONS

Hu et al., Lectin Microarray, Proteomics Clin. Appl., 2009, 3(2), 148-154.*
Gannot, G., et al., "Layered Peptide Array for Multiplex Immunohistochemistry," Journal of Molecular Diagnostics, vol. 9, No. 3, pp. 297-304 (2007).
Olsen, I., et al., "Diffusion blotting for rapid production of multiple identical imprints from sodium dodecyl sulfate polyacrylamide gel electrophresis on a solid support," Journal of Immunological Methods, vol. 220, pp. 77-84 (1998).
Aebersold, R., et al., "Electroblotting onto Activated Glass: High Efficiency Preparation of Proteins from Analytical Sodium Dodecyl Sulfate-Polyacrylamide Gels for Direct Sequence Analysis," The Journal of Biological Chemistry, vol. 261, No. 9, pp. 4229-4238 (1988).
Lee, W., et al., "Protein Array Fabricated by Microcontact Printing for Miniaturized Immunoassay," Journal of Microbiology and Biotechnology, vol. 16, No. 8, pp. 1216-1221 (2006).
Becker, W.M., et al., "Immunological identification and characterization of individual food allergens," Journal of Chromatography B, vol. 756, pp. 131-140 (2001).
Chu, Y., et al., "A Convenient Procedure for Transfer Blotting of Coomassie Blue Stained Proteins from PAGE Gels to Transparencies," Biotechniques, vol. 14, No. 6, pp. 925-930 (1993).
Urlacher, T.M., et al., "Glycoprotein Applications Using Near-Infrared Detection," LI-COR Biosciences (2008).
Rosenfeld, R., et al., "A lectin array-based methodology for the analysis of protein glycosylation," Jounral of Biochemical and Biophysical Methods, vol. 70, pp. 415-426 (2007).
Pilobello, K.T., et al., "Development of a Lectin Microarray for the Rapid Analysis of Protein Glycopatterns," ChemBioChem, vol. 6, pp. 985-989 (2005).
Kuno, A., et al., "Evanescent-field fluorescence-assisted lectin microarray: a new strategy for glycan profiling," Nature Methods, vol. 2, No. 11, pp. 851-856 (2005).
Extended European Search Report corresponding to European Patent Application No. 10382176.5 dated Nov. 5, 2011.
International Preliminary Report on Patentability corresponding to International Patent Application No. PCT/EP2011/060431 dated Dec. 28, 2012.
International Search Report corresponding to International Patent Application No. PCT/EP2011/060431 dated Oct. 14, 2011.

\* cited by examiner

*Primary Examiner* — Maria Leavitt
*Assistant Examiner* — Amy M Bunker
(74) *Attorney, Agent, or Firm* — Jenkins, Wilson, Taylor & Hunt, P.A.

(57) ABSTRACT

The invention relates to a method for identifying in a sample molecules with the capacity to bind to the different members of a molecule library, wherein the molecules which are in the sample are fractionated based on a physicochemical property of the sample and subsequently transferred from the support in which said molecules have been separated to a second support in which the different members of the molecule library are grouped into microarrays such that they uniformly coat the surface of the support. This technique is especially interesting for the identification in a sample of glycoproteins with affinity for a lectin library as well as for the identification of compounds capable of modulating the glycosylation of proteins and for the rapid characterization of alterations in the glycosylation pattern of a sample of proteins, which can be useful in the diagnosis of diseases in which there are alterations in cell glycosylation.

9 Claims, 19 Drawing Sheets ically, to methods for the analysis of glycoproteins based on their capacity to interact specifically with lectins depending on the type of glycosylation.
METHOD FOR THE CHARACTERIZATION OF INTERMOLECULAR INTERACTIONS

CROSS-REFERENCE TO RELATED APPLICATIONS

This application is filed under the provisions of 35 U.S.C. §371 and claims the priority of International Patent Application No. PCT/EP2011/060431 filed on Jun. 22, 2011, and of European Patent Application No. 10382176.5 filed on Jun. 22, 2010. The disclosures of the foregoing international patent application and European patent application are hereby incorporated by reference herein in their respective entireties.

TECHNICAL FIELD OF THE INVENTION

The invention relates to glycoproteins and, more specifically, to methods for the analysis of glycoproteins based on their capacity to interact specifically with lectins depending on the type of glycosylation.

BACKGROUND OF THE INVENTION

Approximately 60% of all proteins are glycoproteins, which makes glycosylation the most important post-translational modification of individual proteins. Glycans have a high degree of microheterogeneity due to the non-encoded action of enzymes responsible for biosynthesis and the processing of glycan structures bound to proteins.

The knowledge of the glycosylation pattern has an increasing interest not only in the field of glycomics, which deals with the high-throughput analysis of glycans and their functions in complex systems, but also for the biotechnological industry, in which the glycosylation of proteins for therapeutic use has to be controlled for regulatory purposes, for optimizing the function and reuptake or for preventing immunogenic reactions. The unique glycoforms of therapeutic proteins with optimized properties are accessible either by means of chemical approaches using purified or synthetic sugars or by means of fermentation in expression systems.

Methods of analysis of glycoproteins based on mass spectrometry, immunotransfer and chromatography are laborious and unsuitable for the rapid and systematic evaluation of the glycosylation state of proteins.

German Democratic Republic patent DD159569B describes a method for the detection of glycosylated proteins which comprises contacting the sample which supposedly contains the glycoprotein to be detected with an array in which a lectin showing affinity for said protein has been immobilized. However, this method only allows the identification based on a single lectin-glycoprotein interaction and does not allow the simultaneous analysis of several lectins or of several glycoproteins.

Pilobello et al. (ChemBioChem 2005, 6, 985-989), Kuno et al. (Nature Methods, 2005, 2:851-856) and Rosenfeld et al. (J. Biochem. Biophys. Methods, 2007, 70:415-426) have described methods for the characterization of the sugars present in a glycoprotein of interest consisting of using a support in which a series of lectins organized in the form of an array have been immobilized and contacting said array with the glycoprotein of interest labeled fluorescently. The terminal sugar content of the glycoprotein can then be determined by means of detecting (either by fluorescence or by fluorescence-assisted evanescent field) of the point of the array at which fluorescence is observed, indicative of the fact that there has been interaction between the lectin and the glycoprotein. However, this method requires previously isolated glycoproteins therefore it is not suitable for characterizing the glycoprotein content of a complex sample.

US20030153013 describe a method for the simultaneous identification of several proteins with the capacity to bind to respective capture proteins which comprises preparing a support in which said capture proteins organized in the form of an array are immobilized. The sample in which the proteins are located is passed through said support and the presence of proteins in the cells of the array in which the capture proteins are immobilized is detected. Nevertheless, this method does not contemplate the possible use of lectins as capture proteins for studying glycoproteins.

WO02083918 describes arrays of carbohydrates for the identification of proteins with affinity for said carbohydrates (lectins).

Nevertheless, there is a need in the art for methods and reagents for the study of glycoproteins which can be applied in complex samples in which there are different glycoproteins.

SUMMARY OF THE INVENTION

In a first aspect, the invention relates to a method for determining the presence in a population of molecules of at least one first member of a binding pair having the capacity to bind specifically to at least one second member of said binding pair which comprises
   (i) fractionating the population of molecules in a first support based on at least one physicochemical property of said first member of the binding pair,
   (ii) transferring the fractionated molecules from said first support to a second support, wherein said second support is uniformly coated by a set of microarrays, wherein each microarray comprises a plurality of second members of the binding pair with different affinity for the first member of the binding pair and wherein said second members of a binding pair are immobilized in said second support,
      wherein the transfer is carried out under conditions suitable for maintaining in the second support the two-dimensional organization of the molecules fractionated in the first support and for allowing the interaction between the molecules of the population of molecules and the at least one second member of the binding pair coinciding spatially in the second support with said molecules and
   (iii) detecting the presence of molecules of the sample in association with at least one second member of the binding pair,
wherein the presence of molecules associated with the second member of the binding pair in at least one of the microarrays is indicative of the presence in the population of molecules of a first member of the binding pair with the capacity to bind specifically to said second member of the binding pair the physicochemical properties of which correspond to the position in the first support coinciding spatially with the array or arrays in which said first member of the binding pair is detected.

In a second aspect, the invention relates to a method for the identification from a plurality of molecules of a second member of a binding pair showing affinity for a first member of said binding pair, wherein said method comprises:
   (i) fractionating a sample comprising said first member of the binding pair in a first support such that the first member of the binding pair is arranged in said first support based on at least one physicochemical property of said first member of a binding pair, (ii) transferring the first member of the binding pair from said first support to a second support, wherein said second support is uniformly coated by a set of microarrays, wherein each of the molecules of the plurality of molecules in which the presence of a second member of the binding pair is to be identified is arranged in each of the cells of the microarray and wherein said plurality of molecules is immobilized in said second support, wherein the transfer is carried out under conditions suitable for maintaining in the second support the two-dimensional organization of the first member of the binding pair fractionated in the first support and for causing the interaction between the first member of the binding pair which is transferred and the second member of a binding pair coinciding spatially in the second support with said protein and (iii) detecting the presence of the first member of the binding pair in association with one or more of the molecules forming the microarrays, wherein the presence of the first member of the binding pair associated with one or several of the molecules immobilized in the second support is indicative of the presence in the mixture of molecules of at least one second member of the binding pair showing the capacity to bind specifically to the first member of the binding pair.

In another aspect, the invention relates to a method for the identification of a cell glycosylation modulator compound which comprises (i) contacting a cell population with the candidate compound,
(ii) obtaining a preparation of proteins of said cell population,
(iii) fractionating the proteins present in said preparation in a first support,
(iv) transferring the fractionated proteins from said first support to a second support, wherein said second support is uniformly coated by a set of microarrays of immobilized lectins, wherein each microarray of lectins comprises at least two different lectins of known specificity, wherein the transfer is carried out under conditions suitable for maintaining in the second support the two-dimensional organization of the proteins of the first support and for causing the interaction between the glycoproteins which are transferred and the lectins of the arrays coinciding spatially with said glycoproteins and
(v) visualizing the presence of glycoproteins at the different points forming the microarrays coinciding spatially in the support with the transferred proteins wherein an alteration in the pattern of glycoproteins of the sample obtained from the cell population treated with the candidate compound in relation to a sample of proteins obtained from a cell population which has not been treated with said compound is indicative of the compound being a cell glycosylation modulator.

In another aspect, the invention relates to a method for the characterization of the specificity of an enzyme capable of modifying the glycans of a glycoprotein which comprises (i) contacting a preparation of glycoproteins with said enzyme under conditions suitable for said enzyme to exert its activity on the glycans forming part of the glycoproteins,
(ii) fractionating the glycoproteins obtained in stage (a) in a first support using at least one physicochemical property of said glycoproteins,
(iii) transferring the fractionated proteins from said first support to a second support, wherein said second support is uniformly coated by a set of microarrays of immobilized lectins, wherein each microarray of lectins comprises at least two lectins of known specificity, wherein the transfer is carried out under conditions suitable for maintaining in the second support the two-dimensional organization of the proteins of the first support and for causing the interaction between the glycoproteins which are transferred and the lectins of the arrays coinciding spatially with said glycoproteins and
(iv) visualizing the presence of glycoproteins at the different points forming the microarrays coinciding spatially in the support with the transferred proteins and
(v) determining the specificity of the enzyme based on the alteration of the pattern of glycoproteins of the sample treated with enzyme in relation to a sample of glycoproteins not treated with said enzyme.

In another aspect, the invention relates to a method for the determination of the presence of a sugar residue in terminal position in the glycans of the glycoproteins of a protein preparation which comprises (i) fractionating the proteins present in said preparation in a first support,
(ii) transferring the fractionated proteins from said first support to a second support, wherein said second support is uniformly coated by a set of microarrays of immobilized lectins, wherein each microarray of lectins comprises at least two different lectins of known specificity, and wherein at least one of said lectins is capable of binding specifically to glycoproteins having said sugar in terminal position of the glycans of said glycoproteins, wherein the transfer is carried out under conditions suitable for maintaining in the second support the two-dimensional organization of the proteins of the first support and for causing the interaction between the glycoproteins which are transferred and the lectins of the arrays coinciding spatially with said glycoproteins and wherein the transfer is carried out in the presence of said sugar and
(iii) visualizing the presence of glycoproteins at the different points forming the microarrays coinciding spatially in the support with the transferred proteins wherein an alteration in the pattern of glycoproteins of the sample obtained in the presence of the sugar with respect to the pattern of glycoproteins obtained when stage (b) has been carried out in the absence of said sugar is indicative of the presence of residues of said sugar in terminal position in the glycans of the glycoproteins.

DETAILED DESCRIPTION OF THE INVENTION

Figure 1:
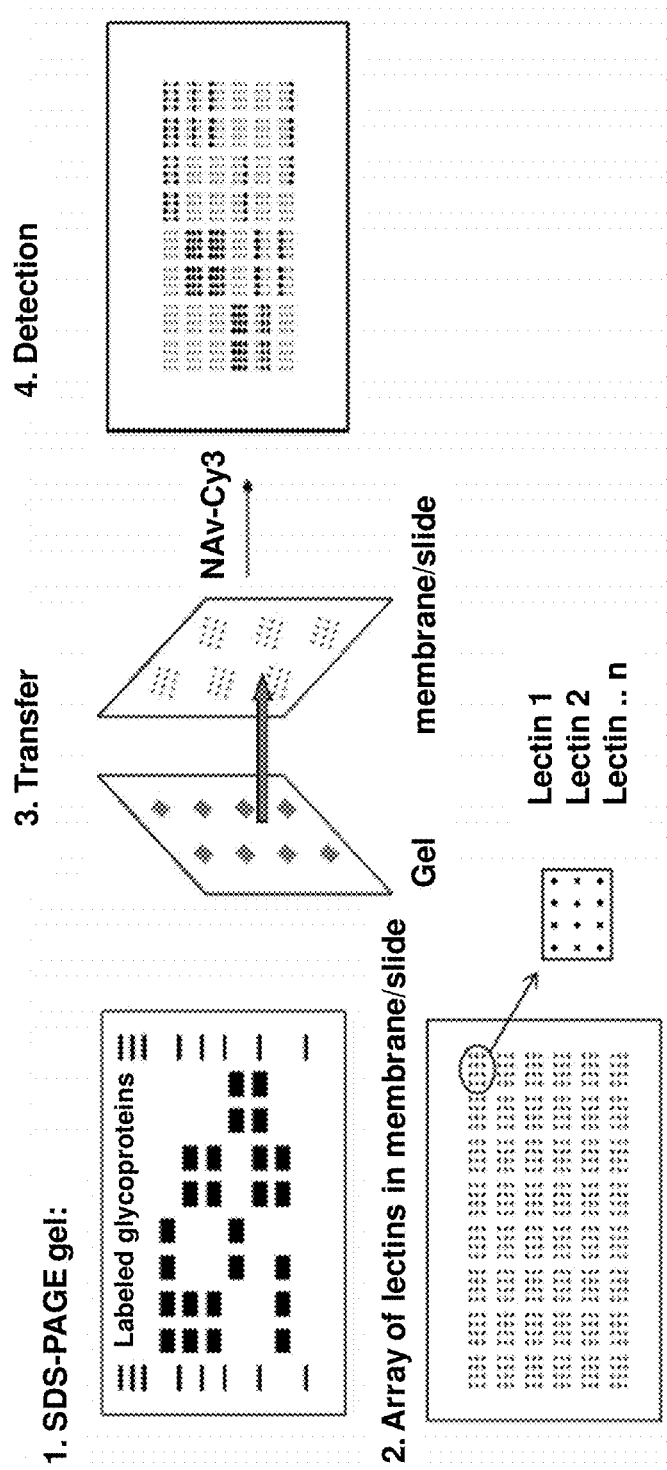
FIG. 1. Schematic depiction of the method of the invention.

The authors of the present invention have developed a technique combining the fractionation of complex protein mixtures in a sample by means of electrophoresis and microarrays of lectins for analyzing glycans present in the glycoproteins of the sample. To that end, the protein mixtures are labeled such that they can be easily visualized (either with a fluorophore or with biotin) and they are separated into one or two dimensions by means of electrophoresis according to their mass and/or isoelectric point. The proteins are then transferred to a suitable support (membrane or glass) on which multiple copies of small arrays of lectins have previously been stamped. The arrays of lectins cover the entire surface in the form of a large array, not unlike a TV screen with 4 different colored pixels for each individual point. A diagram of the method is shown in FIG. 1.

During the transfer process all the proteins in the gel are transferred to the membrane, maintaining their coordinates with respect to the support of the immunotransfer. Given that the transfer membrane has been treated with a blocking agent after stamping the lectins, the non-specific binding of proteins to the membrane is prevented such that the glycosylated proteins are only bound according to their binding affinities for the individual lectins present in the array. During the transfer process, each glycoprotein moves through the gel towards the support and interacts with the individual lectins present in the arrays. For the principle to work, the protein bands in the gel cover at least one entire array of lectins such that all the lectins included in the array are subjected to interaction with the protein which moves from the gel to the membrane.

The glycoproteins bind to the array of lectins through their terminal sugars or sugar epitopes recognized by the individual lectins. The other non-glycosylated proteins cannot bind to the support and are removed in the washing step. The visualization of the proteins bound to the arrays of lectins and the glycosylation pattern thereof depends on the type of labeling applied to the proteins of the initial mixture, such that if the proteins have been labeled with a fluorophore, they are directly visualized by means of illuminating the support at the excitation wavelength of said fluorophore whereas if the proteins have been labeled with biotin, they are visualized by means of previously incubating the support with streptavidin labeled with a fluorophore, washed again and examined with a fluorescence microscope or a gel viewer (for example, versa-doc, Biorad). The individual arrays are immediately identified by one or more control spots (where biotinylated lectins have been stamped). The intensities for the individual spots depend on the amount and the strength of the sugar-lectin interactions. The type of sugar is defined by the position of the lectin interacting in the array.

Thus, multiple glycoproteins can be analyzed simultaneously in individual arrays of lectin in the membrane and their glycan composition can be evaluated. Given that the change of glycosylation is frequently a specific characteristic of a disease, type of tissue, species, age or development state, it is possible to use the method of the present invention to easily identify and follow this type of process.

Nevertheless, the method developed in the present invention can be used not only for the characterization of the glycans present in a glycoprotein or mixture of glycoproteins but also, more generally, for the study of any type of interaction between any two molecules provided that there is a specific binding between both molecules. Thus, the method of the invention allows determining the presence in a sample of molecules with the capacity to bind to a second molecule or determined set of molecules, with the added value that the detection of the molecules in the sample with the desired affinity is accompanied by information about the physico-chemical properties of said molecules since it is possible to deduce from the array in which the signal is detected the values of the parameters in the physicochemical properties with which the proteins have been fractionated in the first stage. Likewise, the method of the invention allows identifying from a collection of reagents those which have affinity for a determined molecule.

Method for Analyzing the Presence in a Sample of at Least One Protein Having the Capacity to Bind Specifically to at Least One Reagent The method of the invention is useful for the identification in a complex sample of molecules of those with the capacity to bind to one or several determined reagents. For this purpose, the starting materials will be a sample formed by a more or less complex mixture of molecules in which the presence of a molecule (first member of a binding pair) with affinity for one or several molecules (second members of a binding pair) is to be detected and a microarray formed by one or several molecules against which molecules with affinity are to be found. This method would have the additional advantage that, in addition to identifying the presence in the sample of molecules with affinity for the reagent, it would allow a preliminary characterization of the molecules showing said affinity since the relative position in the second support of the array in which the molecules are detected allows determining the value of the physicochemical parameter which was initially used to separate the molecules since when the transfer of the first to the second support is performed, there is a correspondence between position in the first support (depending on the physicochemical properties) and position in the second support.

Thus, in a first aspect, the invention relates to a method for determining the presence in a population of molecules of at least one first member of a binding pair having the capacity to bind specifically to at least one second member of said binding pair which comprises (i) fractionating the population of molecules in a first support based on at least one physicochemical property of said first binding pair, (ii) transferring the fractionated molecules from said first support to a second support, wherein said second support is uniformly coated by a set of microarrays, wherein each microarray comprises a plurality of second members of the binding pair with different affinity for the first member of the binding pair and wherein said second members of a binding pair are immobilized in said second support, wherein the transfer is carried out under conditions suitable for maintaining in the second support the two-dimensional organization of the molecules fractionated in the first support and for allowing the interaction between the molecules of the population of molecules and the at least one second member of the binding pair coinciding spatially in the second support with said molecules and (iii) detecting the presence of molecules of the sample in association with at least one second member of the binding pair, wherein the presence of molecules associated with the second member of the binding pair in at least one of the microarrays is indicative of the presence in the population of molecules of a first member of the binding pair with the capacity to bind specifically to said second member of the binding pair the physicochemical properties of which correspond to the position in the first support coinciding spatially with the array or arrays in which said first member of the binding pair is detected.

As used in the present invention, the term "molecule" refers to any particle formed by a stable set of at least two covalently bonded atoms against which a second molecule with affinity for said molecule is to be identified.

The term "binding pair" refers to a couple of molecules (referred to first and second member of the binding pair) having the capacity to bind specifically by means of any type of intermolecular interaction including but not limited to biochemical, physiological and/or chemical interactions. The binding pair includes any type of interaction of immune type such as antigen/antibody, antigen/antibody fragment, hapten/anti-hapten as well as interactions of non-immune type such as avidin/biotin, avidin/biotinylated molecules, folic acid/folate-binding protein, hormone/hormone receptor, lectin/carbohydrate, lectin/molecule modified with carbohydrates, enzyme/enzyme substrate, enzyme/enzyme inhibitor, protein A/antibody, protein G/antibody, complementary nucleic acids (including sequences of DNA, RNA and peptide nucleic acids (PNA)), polynucleotide/polynucleotide-binding protein and the like.

As used in the present invention, the expression "specific binding" refers to the capacity of a first molecule to bind specifically to a second molecule by means of the existence of complementarity between the three-dimensional structures of the two molecules with a substantially higher affinity for non-specific binding such that the binding between said first and second molecule preferably takes place before the binding of any of said molecules with respect to the other molecules present in the reaction mixture. It is understood that there is high affinity in the binding of two molecules when the complex resulting from said binding has a dissociation constant (KD) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M or less than $10^{-15}$ M.

The terms "bond" and "binding" are used indistinctly to refer to an interaction between two or more entities. In those cases in which two entities are bound to one another, they can be directly bound (for example, by means of covalent bonds, ionic forces, hydrogen bonds, electrostatic interactions, Van der Waals forces or a combination of the above) or they can be indirectly bound, for example, by means of a linker.

In a first stage, the method of the invention involves fractionating the molecules present in the sample in a first support based on at least one physicochemical property of said molecules.

The starting samples for their study in the method of the present invention include any type of sample in which the presence of molecules with affinity for a second member of a determined binding pair is to be detected. Thus, the invention contemplates the use of samples coming from the excretion or secretion by any live organism, including prokaryotic or eukaryotic organisms, clinical samples obtained both from a healthy subject or apparently healthy and from a patient affected by a determined disorder or disease. The clinical samples from a human or animal can be obtained from any organ or tissue (including a biopsy or autopsy sample such as a tumor biopsy) or can comprise a cell (either a primary cell or from cultured cells) or medium conditioned by any cell, tissue or organ.

As used in the present invention, the term "fractionating" involves depositing the mixture of molecules in a support and subjecting said support to conditions allowing the different molecules of the mixture to migrate in said support along one or two axes based on at least one physical or chemical property of the molecules of the sample. Physicochemical properties of the molecules allowing their separation include the molecular weight, the isoelectric point and the hydrophobicity. Suitable methods for the separation of proteins include thin layer chromatography, isoelectric focusing, HPLC, FPLC, molecular filtration, ion exchange chromatography, reversed-phase chromatography or affinity chromatography. The person skilled in the art will understand that the type of fractionation will depend on the type of molecule which is being analyzed. Thus, in the particular case that the sample which is to be analyzed is a preparation of proteins, the latter are fractionated based on their molecular weight, their electric charge and/or their acid/base properties.

The terms "protein" and "polypeptide" are used in an equivalent manner in the present invention and refer to polymeric forms of any length and which can include both encoded and non-encoded amino acids, chemically or biochemically modified amino acids and polypeptides with modified backbones. Likewise, the term includes fusion proteins including but not limited to proteins with a heterologous sequence, fusions with heterologous and native signal sequences, polypeptides with and without methionine residues in N-terminal position, immunologically labeled proteins and proteins fused to detectable residues.

In an even more preferred embodiment, the members of the binding pair are a glycoprotein and a lectin.

As used in the present invention, the term "glycoprotein" refers to any protein which is covalently modified by at least one carbohydrate residue. Glycoproteins which can be studied according to the method of the invention include those which are modified by a monosaccharide or by an oligosaccharide and in which said monosaccharide or oligosaccharide is bound to the polypeptide chain by a side chain comprising a nitrogen atom (N-glycosylation) or an oxygen atom (O-glycosylation). Typically, N-glycosylation comprises the modification of proteins in asparagine residues which form part of a consensus sequence of the Asn-X-Ser or Asn-X-Thr type. O-glycosylation occurs in the side chains of serine and/or threonine residues.

The term glycoprotein does not intend to be limiting in terms of the length of the polypeptide chain, therefore glycopeptides are considered as glycoproteins for the purposes of the present invention.

Typical monosaccharides which can form part of a glycoprotein include but are not limited to glucose (Glu), galactose (Gal), mannose (Man), fucose (Fuc), N-acetylneuraminic acid (Neu5Ac) or another sialic acid, N-acetylglucosamine (GlcNAc), N-acetylgalactosamine (GalNAc), xylose (Xyl) and derivatives thereof (for example, phosphoderivatives).

Oligosaccharides which can form part of an N-glycosylated glycoprotein include oligosaccharides with high mannose content, complex oligosaccharides and hybrid type oligosaccharides. Oligosaccharides with high mannose content refer to chains comprising two N-acetylglucosamine residues with a variable number of mannose or mannosyl phosphate residues but typically without any other type of monosaccharides. Complex N-glycosylation refers to structures typically comprising one, two or more (up to five) external branches with a sialyl-lactosamine sequence, frequently coupled to an internal $Man_3GlcNAc_2$ structure which appears in a conserved manner in all N-glycans. For example, a complex N-glycan can have at least one branch or at least two branches of alternate residues of GlcNAc and galactose (Gal) or sialic acid which can end in a variety of oligosaccharides but which typically do not end with a mannose residue. On the other hand, hybrid type glycosylation refers to intermediate forms between the two previous ones in which the glycoproteins have terminal and non-terminal mannose residues in addition to the two N-acetylglucosamine residues. In contrast to complex glycosylation, in hybrid type glycosylation, at least one of the oligosaccharide chains ends in a mannose residue. Although this classification is frequently used to describe naturally occurring glycans in glycoproteins, it is understood that synthetic or non-naturally occurring glycans can be described in the same manner. Thus, an N-glycan comprising a single galactose chain and sialic acid connected to a simple GlcNAc residue would be a complex sugar, even if it lacks the $Man_3GlcNAc_2$ core.

Glycoproteins or glycopeptides can additionally or alternatively be modified by glycans bound through the side chains of the amino acids serine and threonine (O-glycosylation). O-glycosylation comprises adding a first sugar residue which can be N-acetylgalactosamine, xylose, N-acetylglucosamine, glucose, fucose, mannose or galactose by means of a glucosyltransferase. After adding the first monosaccharide, the O-glycan is elongated by means of adding individual monosaccharides, giving rise to different types of structures depending on the monosaccharide known as "Core 1", when the monosaccharide is galactose, "Core 2" resulting from adding N-acetylglucosamine to the "Core 1" structure, "Core 3" when the monosaccharide is N-acetylglucosamine and "Core 4" resulting from adding a second N-acetylglucosamine residue to the "Core 3" type structure.

As used in the present invention, the term lectin refers to any protein different from an antibody and which is capable of binding to a carbohydrate or to a structure modified by a carbohydrate, including glycoproteins and glycosylated nanostructures. Although most immobilized lectins are derived from plants, in the present invention the term lectin is used to refer to any protein different from an antibody with the capacity of binding to sugars coming from any organism as well as variants thereof obtained in a recombinant manner and which maintain the capacity of binding to the sugar residues in glycoproteins. Examples of lectins suitable for use in the present invention include but are not limited to lectins isolated from *Conavalia ensiformis, Anguilla anguilla, Tritium vulgaris, Datura stramonium, Galanthus nivalis, Maackia amurensis, Arachis hypogaea, Sambucus nigra, Erythtina cristagalli, Lens culinaris, Glycine max, Phaseolus vulgaris, Allomyrina dichotoma, Dolichos biflorus, Lotus tetragonolobus, Ulex europaeus,* and *Ricinus communis*.

Examples of lectins suitable for use in the present invention include but are not limited to the lectins shown in Table 1, which indicates the common name of the lectin, the organism which it comes from and the sugar which binds specifically to said lectin.

| Lectin | Origin | Specificity |
| --- | --- | --- |
| ConA | *Canavalia ensiformis* | Glycans rich in mannose and terminal GLc-R |
| Lectin I-B | *Griffonia simplicifolia* | α1-3 Galactose (R) |
| Lectin II | *Griffonia simplicifolia* | α or 1β terminal GlcNAc (R) |
| RCA-I | *Ricinus communis* | Terminal GalβGlcNAc-R |
| Wheat germ agglutinin | *Triticum vulgaris* | Terminal sialic acid and terminal GlcNAc |
| UEA-I | *Ulex europaeus* | Terminal Fucα1-2Galβ1-R |
| WFA | *Wisteria floribunda* | GalNAcα/β-R |
| LFA | *Limax flavus* | Terminal sialic acid |
| Eel lectin | *Anguilla anguilla* | Fu(Galcα1-2 and Fucα1-4 |
| Peanut agglutinin | *Arachis hypogaea* | Galβ3GalNAcα1-Ser/Thr |
| Stramonium agglutinin | *Datura stramonium* | (Galβ4GlcNAc)n-R |

-continued

| Lectin | Origin | Specificity |
| --- | --- | --- |
| Cockspur coral tree lectin | Erythrinia cristagalli | (Galβ4-R) |
| Snail lectin | Helix pomatia | GalNAcα1-R |
| Lotus lectin | Lotus tetragonolobus | Fucα1-3/GalNAc-R |
| Tomato lectin | Lycopersicum esculentum | (Galβ4GlcNAc)n-R |
| MAL/MAA | Maackia amurensis | 2-3Galβ3GalNAc-R sialic acid |
| L-PHA | Phaseolus vulgaris | tri/tetraantennary N-glycans |
| E-PHA | Phaseolus vulgaris | Bisected biantennary N-glycans |
| Pea lectin | Pisum sativum | tri/bi nuclear fucosylated N-glycans |
| Elder lectin | Sambucus nigra | 2-6Gal/Gal (/GalNAc sialic acid |
| Potato lectin | Solanum tuberosum | Long chain (Galβ4GlcNAc)n-R |
| Black-eyed pea lectin | Dolichos biflorus | GalNAcα1-R |
| Lentil lectin | Lens culinaris | Fucosylated central region of complex bi- and triantennary N-glycans |
| Snowdrop lectin | Galathus nivalis | α1-3 and α1-6 Mannose |
| Hairy vetch lectin | Vicia villosa | GalNAcα-Ser/Thr |
| Jacalin | Artocarpus integrifolia | (Sia)Galβ1-3GalNAcα1-Ser/Thr |
| Aleuria aurantia lectin | Aleuria aurantia | Fucα1-2Galβ1-4(Fucα1-3/4)Galβ1-4GlcNAc; $R_2$-GlcNAcβ1-4(Fucα1-6)GlcNAc-$R_1$ |
| Soybean lectin | Glycine max | Gal/GalNAcα-R, Gal/GalNAcβ-R |
| Alomyrina dichotoma lectin | Allomyrina dichotoma | Galβ1-4GlcNAc-R |

The terms "antibody" and "immunoglobulin" refer to antibodies and immunoglobulins of any isotype, antibody fragments which maintain the capacity to bind to the antigen, including but not limited to Fab, Fv, scFv, Fab', Fv, F(ab')2 and Fd fragments, chimeric antibodies, humanized antibodies, single chain antibodies and fusion proteins comprising the antigen-binding region of an antibody.

In a preferred embodiment, the proteins of the sample have been covalently modified such that their subsequent detection is possible. In principle, the invention contemplates the use of any label provided that the covalent conjugation to the proteins of the sample is possible and that it allows the subsequent detection of said proteins. Thus, the invention contemplates the possibility of modifying the proteins with a radioisotope of the type of $^{3}$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At or $^{213}$B. The labeling with radioisotopes is typically carried out by means of using chelating ligands which are capable of complexing metal ions such as DOTA, DOTP, DOTMA, DTPA and TETA (Macrocyclics, Dallas, Tex.).

Nevertheless, in a preferred embodiment, the proteins are labeled with a fluorescent group. The fluorescent group can bind to the side chains of amino acids directly or through a connecting group. Preferably, the fluorescent groups which are used to label the proteins of the sample must be (i) groups giving a good signal in the absence of background, (ii) stable groups which allow detecting the signal without significant photobleaching, (iii) groups having good solubility in aqueous media to facilitate the labeling process and/or (iv) groups which are not toxic or alter the proteins such that they lose the capacity to bind to their targets. Methods for conjugating fluorescent reagents to polypeptides are well known in the state of the art and have been described, for example, in Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al. (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGryter, Berlin and New York; and Wong (1991) Chemistry of Protein Conjugation and Cross-linking, CRC Press, Boca Raton, Fla.); De Leon-Rodriguez et al. (2004) Chem. Eur. J. 10:1149-1155; Lewis et al. (2001) Bioconjugate Chem. 12:320-324; Li et al. (2002) Bioconjugate Chem. 13:110-115; Mier et al. (2005) Bioconjugate Chem. 16:240-237.

Suitable reagents for labeling polypeptides with fluorescent groups include chemical groups showing the capacity to react with the different groups appearing in the side chains of the proteins, including amino groups and thiol groups. Thus, chemical groups which can be used to modify the proteins according to the present invention include but are not limited to maleimide, haloacetyl, iodoacetamide, succinimidyl ester (for example, NHS, N-hydroxysuccinimide), isothiocyanate, sulfonyl chloride, 2,6-dichlorotriazinyl, pentafluorophenyl ester, phosphoramidite and the like.

A suitable reactive functional group for use in the present invention is the N-hydroxysuccinimide (NHS) ester of a detectable group modified with a carboxyl group. The carboxyl group modifying the fluorescent compound is typically activated by means of contacting said compound with a carbodiimide reagent (for example, dicyclohexylcarbodiimide, diisopropylcarbodiimide, or an uroniyum reagent such as TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator of the type of 1-hydroxybenzotriazole (HOBt) and N-hydroxysuccinimide to give rise to the NHS ester of the label.

Suitable fluorescent compounds for use in the present invention include but are not limited to ethidium bromide, SYBR Green, fluorescein isothiocyanate (FITC), tetramethyl rhodamine isothiol (TRIT), 5-carboxyfluorescein, 6-carboxyfluorescein, fluorescein, HEX (6-carboxy-2',4,4',5',7,7'-hexachlorofluorescein), Oregon Green 488, Oregon Green 500, Oregon Green 514, Joe (6-carboxy-4',5'-dichloro-2',7'-dimethoxyfluorescein), 5-carboxy-2',4',5',7'-tetrachlorofluorescein, 5-carboxyrhodamine, rhodamine, tetramethylrhodamine (Tamra), Rox (carboxy-X-rhodamine), R6G (rhodamine 6G), phthalocyanines, azomethines, cyanines (Cy2, Cy3 and Cy5), Texas Red, Princeton Red, BODIPY FL-Br2, BODIPY 530/550, BODIPY TMR, BODIPY 558/568, BODIPY 564/570, BODIPY 576/589, BODIPY 581/591, BODIPY TR, BODIPY 630/650, BODIPY 650/665, DABCYL, Eosin, Erythrosine, ethidium bromide, green fluorescent protein (GFP) and the analogs thereof, inorganic fluorescent labels based on semiconductor nanocrystals (Quantum dot), fluorescent labels based on lanthanides such as $Eu^{3+}$ and $Sm^{3+}$ and the like.

In a preferred embodiment, the proteins are labeled by means of the conjugation with a first member of a binding pair before the fractionation thereof. In an even more preferred embodiment, said covalent modification is a biotinylation. As used in the present invention, the term "biotinylation" refers to the covalent binding of biotin to a molecule (typically a protein). The biotinylation of the proteins of the sample is carried out using reagents capable of conjugating biotin to the side chain of the proteins, wherein said conjugation fundamentally takes place in the primary amino groups and in the thiol groups appearing in the side chains of the proteins. Suitable reagents for the biotinylation of amino groups include molecules containing biotin and a group capable of reacting with amino groups such as succinimide esters, pentafluorophenyl ester or alkyl halides, the biotin group and the reactive group being separated by a spacer of any length (for example, of 8-40 A in length). Some examples of these biotinylation agents include NHS-biotin agents (containing an ester bond of five carbon atoms between the biotin and the NHS group), sulfo-NHS-biotin, NHS-LC-biotin, sulfo-NHS-LC-Biotin, NHS-LC-LC-biotin, sulfo-NHS-LC-LC-biotin, sulfo-NHS-SS-biotin, NHS-PEO4-biotin, PFP-biotin, TFP-PEO-biotin and the like, wherein "NHS" indicates a N-hydroxysuccinimide group, "LC" refers to an amide type bond of 6 carbon atoms located between the NHS group and the biotin, "PEO" refers to a ethylene oxide group, wherein the subscript indicates the number of PEO units, "PFP" refers to a pentafluorophenyl group, "TFP" refers to a tetrafluorophenyl group, "sulfo" refers to a sulfonate group (SO3" Na+) and "SS" refers to a disulfide group. Examples of biotinylation reactive agents with thiol groups include molecules comprising biotin and a group of the maleimido or alkyl halide type, separated by a spacer of any length. Examples of biotinylation reagents include maleimide-PEG-biotin, biotin-BMCC (containing an N-terminal maleimido group and a cyclohexyl group, 2 amide bonds and 9 linking carbon atoms), PEO-iodoacetyl biotin, iodoacetyl-LC-biotin, biotin-HPDP (containing a pyridyl disulfide group) and the like.

The suitable support for the fractionation of proteins in the sample may be chosen by the person skilled in the art depending on the type of molecule which is to be transferred. In the even that the sample to be analyzed is a population of protein, the first support can be, but is not limited to, polyacrylamide, agarose or gelatin.

In a preferred embodiment, the molecules of the population are fractionated by means of electrophoresis. As used in the present invention, the expression "electrophoresis" refers to a process in which the charged molecules are separated in a determined medium (for example, an electrolyte solution) under the effect of an electric field. The charged molecules thus migrate through a separation medium (the positively charged molecules migrate towards the cathode and the negatively charged molecules migrate towards the anode) and are separated into bands due to the different mobilities of said molecules in the separation medium.

In a preferred embodiment, the fractionation by means of electrophoresis of the molecules of the sample is carried out by means of gel electrophoresis. In the event that the molecules object of study are proteins, said electrophoresis can be carried out under native conditions or under denaturing conditions, the latter mode being preferable. To that end, the sample containing the proteins is treated with a buffer containing a detergent, preferably sodium dodecyl sulfate (SDS). The detergent denatures the proteins and binds to them by a number which is proportional to the length of the protein. Given that the length of an unfolded protein is proportional to its molecular weight, the number of detergent molecules which are associated with the protein is proportional to the molecular weight. In the event that SDS is used, since it is a negatively charged molecule, the different proteins will have similar mass-charge ratio values but will migrate in a differential manner depending on the size of the protein because the gel in which the separation is carried out works like a molecular sieve such that the migration of the proteins depends on the friction thereof with the gel, such friction being greater the larger the size of the protein. Gel electrophoresis is preferably carried out using crosslinked acrylamide (polyacrylamide), such that an increase in the percentage of polyacrylamide in the gel results in a reduction of the size of the resulting pores, which causes a delay in the mobility of the molecule relative to a gel with a lower percentage of polyacrylamide (larger pore size).

In another preferred embodiment, the proteins are fractionated by means of two-dimensional electrophoresis. As used in the present invention, the term "two-dimensional electrophoresis" refers to the separation of a mixture of molecules based on two physical properties thereof. In a preferred embodiment, the separation of proteins by means of two-dimensional electrophoresis is carried out according to the isoelectric point of said proteins (first dimension) and according to the molecular weight (second dimension), the separation in the first dimension being in a direction aimed at about 90° with respect to the first one. For the purpose of separating proteins based on their isoelectric point, the sample is applied to a gel containing a pH gradient and an electric potential is applied through the gel. Given that all the proteins have a net charge different from zero when they are at a pH different from that of the isoelectric point, the positively charged proteins will migrate towards the most negative end of the gel, if they are negatively charged, they will migrate towards the most positive end of the gel such that they will accumulate in the region of the gel in which the pH coincides with their isoelectric point. Before separating the proteins based on their molecular weight, the gel in which the proteins have been separated based on the pI is treated with sodium dodecyl sulfate (SDS) and other reagents. In the second dimension a potential difference is again applied, but with an angle of 90° with respect to the first electric field. The proteins will thus be attracted to the positive side of the gel in a manner proportional to their mass-charge ratio. The gel in which the separation is carried out works like a molecular sieve such that the migration of the proteins depends on the friction thereof with the gel, such friction being greater the larger the size of the protein.

In a second stage, the first method of the invention comprises transferring the fractionated molecules from the support in which said fractionation has been performed (first support) to a second support, wherein said second support is uniformly coated by a set of microarrays and wherein each microarray comprises at least one second member of a binding pair and wherein said second member of a binding pair is immobilized in said second support and wherein the transfer is carried out under conditions suitable for maintaining in the second support the two-dimensional organization of the proteins of the first support and for causing the interaction between the molecules of the population and the at least second member of a binding pair forming part of the arrays and coinciding spatially with said proteins.

The conditions suitable for carrying out the transfer can be determined by the skilled person in a routine manner by varying the different parameters which affect the transfer efficiency and which include but are not limited to the local concentration of the molecules in the first support, the transfer time, the force which is applied and the affinity shown by the molecules of the sample for the second members of the binding pair which are immobilized in the second support. In the event that the immobilized proteins are lectins, the transfer efficiency will depend on the degree of glycosylation of the proteins of the sample and, more particularly, on the interaction between the glycans of the protein with the individual lectins.

As used in the present invention, the term "transferring" refers to treating the support in which the molecules have been fractionated such that such molecules migrate perpendicular thereto, leaving said first support towards a second support arranged in contact with the first support and the surface of which is capable of retaining said molecules. A determined percentage of the molecules which were in the first support thus pass to the second support. The molecules are transferred from the first to the second support by using methods well known to the skilled person. In the particular case of transferring proteins, the transfer is carried out by passing an electric field through the first and second support, both supports being in contact as was originally described by Towbin, H., et al. (Proc. Natl. Acad. Sci. USA, 1979, 76: 4350) and Stott, D. I., (J. Immunol. Methods, 1989, 119:153-187). The transfer can be carried out using a wet transfer device or a semi-dry device as described in U.S. Pat. No. 6,592,734. In the most typical case in which the first support is a gel and the second support is a membrane, the surface of the membrane is wetted with the buffer solution in which the transfer is to be carried out and contacted with the gel, preventing air bubbles between the gel and the membrane.

The transfer can be carried out by means of electrophoresis, for which the gel-membrane combination is placed in an electrotransfer device which has a cathode and an anode and which is filled with the transfer buffer. An electric field is then applied for the time sufficient for the proteins to be entrained from the gel towards the membrane in which they are retained as a result of the interaction of said membrane with the proteins. The time during which the transfer is carried out and the voltage applied fundamentally depends on the thickness of the gel and on the molecular weight of the proteins object of the study.

Alternatively, it is possible to transfer the fractionated molecules in the first support to the second support in the absence of electric field by simple diffusion, which has the advantage of preventing the lateral diffusion of the proteins, which is particularly important for the method of the present invention wherein it is important to identify with precision the cell of the microarray in which the signal is detected. Diffusion transfer is carried out using methods known to the skilled person such as the methods described by Olsen et al. (Journal of Immunological Methods 1998, 220:77-84) and by Kurien et al. (Journal of Immunological Methods, 2003, 274:1-15). The transfer is carried out by washing the gel in which the proteins have been fractionated with acetic acid/MeOH for the purpose of preventing the diffusion of the bands during the transfer and it is contacted with the support in the presence of the transfer buffer for a suitable time to allow the fractionated proteins in the gel to diffuse to the support. Diffusion transfer is the method of choice in those cases in which electrotransfer cannot be used, as occurs, for example, when the support which is coated with arrays of lectins is made of a non-conductor material (for example, glass).

Diffusion transfer allows performing several transfers of the same gel to membranes or slides which contain, for example, different microarray densities, or microarrays of different composition.

The transfer efficiency can be evaluated by means of using techniques which allow detecting the presence of proteins in the membrane. In the event that the fractionated proteins have been fluorescently labeled, the evaluation of the transfer performance of the proteins from the first support to the second support is carried out by means of visualization of the fluorescence emitted by the membrane when it is irradiated at a wavelength which corresponds to the excitation wavelength of the fluorophore which has been used to label the proteins. If the proteins have been labeled with a label which is not directly detectable (for example, if the proteins of the mixture have biotinylated), the transfer performance can be evaluated by means of staining the first support with reversible stains which show affinity for proteins such as Ponceau S, Alcian Blue 8GX, amido Black, Eosin Y, Fast Green FCF, Fluorescamine and Sudan Black B, such that if the transfer has been positive, the first support must be substantially free of proteins. Suitable stains for their use in the present invention for detecting the (absence of) proteins in the first support after the transfer include but are not limited to reversible or irreversible stains showing affinity for proteins such as Ponceau S, Alcian Blue 8GX, amido Black, Eosin Y, Fast Green FCF, Fluorescamine and Sudan Black B.

Alternatively, since the transfer of proteins from the first to the second support is partial, particularly when the diffusion transfer technique is used, it is possible to visualize the proteins in the first support by means of staining the latter with any of the stains aforementioned. Thus, the visualization of all the molecules of the starting sample fractionated in the first support allows performing an overlap with the signal which is observed in the second support, which allows identifying the molecules interacting with the immobilized molecules more easily.

As used in the present invention, the term "support" refers to any solid material to which the components of the invention are physically bound, thus being immobilized. Solid supports suitable for their use in the present invention include but are not limited to silicone, glass, quartz, polyimide, acrylate, polymethylmethacrylate, ceramic, nitrocellulose, metals, amorphous silicon carbide, polystyrene as well as any other material suitable for micromanufacture or microlithography.

The components can be immobilized to the support by means of covalent bonds or by means of non-covalent bonds such as hydrogen bridges, hydrophobic interactions or ionic bonds. A general review of suitable microarrays and of supports has been described in Shalon et al. (Genome Research 6: 639-645 (1996)), LeGendre (BioTechniques 9: 788-805 (1990)), U.S. Pat. Nos. 6,197,599 and 6,140,045. Alternatively, it is possible to use supports activated by means of epoxy groups, vinyl sulfonic groups, active ester groups, aldehyde groups, carboxyl groups, amino groups, thiol groups, isothiocyanate groups and the like. In the event that the support is activated by means of epoxy groups, these groups include 3-glycidoxypropyltrimethoxysilane (GTMS), 2-(3,4-epoxycyclohexyl)ethyltrimethoxysilane, 3-glycidoxypropylmethyldiethoxysilane, 3-glycidoxypropyltriethoxysilane and the like.

The present invention requires the use of solid supports in which one or several second members of the binding pair have been immobilized regularly organized in microarrays which substantially and uniformly coat the entire surface of the support. In the preferred case that the second members of the binding pair are lectins (when the presence of glycoproteins in a sample is to be identified), the microarrays contain a single lectin or, more preferably, several lectins of different specificity. To that end, it is necessary to apply controlled amounts of each lectin solution to preselected sites of the support. In the present invention, the particular method which is used for the application of the solutions to the support is not essential provided that said method allows administering constant amounts of the lectin solution and that the application can be carried out in a controlled manner such that the arrays are regular.

Thus, the manual application of an aliquot of the lectin solution to a predetermined point of the support is possible. Examples of methods used for manually applying a liquid solution to a membrane includes the dot blot method, in which a device with multiple wells comprising solutions of the different lectins which are to be immobilized are passed through the membrane by means of applying a vacuum. A variant of the dot blot technique is the so-called slot blot, in which the wells of the device are oval shaped.

Alternatively, it is also possible to obtain microarrays in a support by means of using an array of applicators which are immersed in the wells of a device comprising solutions of the different lectins to be applied (for example, a multiwell plate with 96 wells). The applicators are subsequently contacted with the support such that drops of each of the solutions are transferred to the support, the same order being maintained as in the multiwell plate. This technique allows transferring proteins to a membrane repeatedly, which allows creating a membrane with 9216 points in a region of 22×22 cm (Lehrach, et al., Hybridization Fingerprinting in Genome Mapping and Sequencing, Genome Analysis, Vol. 1 (Davies and Tilgham, Eds.), Cold Spring Harbor Press, pp. 39-81 (1990)).

Another method for generating an array of compounds of interest (lectins) in a support involves dispensing a known volume of a reagent in each of the positions of the array by means of using capillary dispensers and repeating the process with suitable solutions for each position of the array until obtaining the array. This method can be carried out for forming a plurality of arrays in which the stage of depositing the solution is carried out repeatedly in each of the support regions in which an array of immobilized proteins is to be created. This method has been described in detail in U.S. Pat. No. 5,807,522, incorporated herein by reference.

Alternatively, the application of the lectin solution to the support can be carried out by means of injection printing or any other type of "drop-on-demand" device as have been described by Brennan (U.S. Pat. No. 5,474,796), Tisone (U.S. Pat. No. 5,741,554), and Hayes et al. (U.S. Pat. No. 5,658,802), the content of which is incorporated herein by reference.

Another possibility involves the use of devices similar to those which are used for printing on paper. For example, a solution of a lectin of interest can be loaded in the head of an inkjet printer and printed on suitable membranes. In a preferred embodiment, the printing is piezoelectric, in which a piezoelectric ceramic transducer to which there is applied a voltage is used, resulting in a modification of the shape of the transducer in the head which results in the occurrence of a vacuum which is filled with the solution to be printed. When the voltage is removed, the ceramic expands to an original shape, which results in the ejection of a drop of liquid from the head. Nevertheless, the printing method using an inkjet is not limited to the use of piezoelectric printing but rather includes the use of other types of heads, such as thermal, electrostatic and acoustic droplet heads.

Alternatively, it is possible to use substrates activated by means of epoxy groups, vinyl sulfonic groups, active ester groups, aldehyde groups, carboxyl groups, amino groups, thiol groups, isothiocyanate groups and the like. In the event that the support is activated by means of epoxy groups, these groups include 3-glycidoxypropyltrimethoxysilane (GTMS), 2-(3,4-epoxycyclohexyl)ethyltrimethoxysilane, 3-glycidoxypropylmethyldiethoxysilane, 3-glycidoxypropyltriethoxysilane and the like.

In a preferred embodiment, the support in which the lectins are immobilized is a glass support which is coated with a hydrogel and in which the carboxylate groups of the support are activated as active ester with NHS, which allows the covalent conjugation of the lectins. Supports of this nature are commercially available, such as, for example, the Nexterion slide H of Schott (http://www.us.schott.com/nexterion/english/products/coated_slid es/thin_film/slide_h/slide_h.html). This type of slide is characterized by having low background fluorescence, a high immobilization capacity, and the stabilizing effect for biomolecules in the three-dimensional polymeric layer by a 3D polymeric layer forming a hydrogel.

In a preferred embodiment, the support in which the lectins are immobilized (second support) is a membrane. As used in the present invention, the term "membrane" refers to any type of flexible sheet of a polymeric or elastomeric nature. Particular aspects of the membranes to be optimized for their use in the present invention include the capacity of the membrane of binding high amounts of protein per surface unit, protein binding capacity with minimum denaturation of said protein and the protein binding incapacity when said proteins are transferred from another support. Another interesting aspect of the membrane for its use in the method of the present invention is that it has a minimum degree of absorption. This property allows, when the lectin is immobilized by means of applying a drop of solution containing said lectin and is left to dry, maintaining the drop of lectin substantially limited to the site of application which allows using drops of a smaller volume and obtaining points of immobilized lectin of a small diameter, which allows obtaining smaller sized arrays. In contrast, when the membrane has a high absorption, the drops of lectin solution which are applied give rise to larger sized and more diffuse points of immobilized lectin.

Examples of membranes suitable for their use in the present invention include but are not limited to any type of material which has been used previously for Northern blot, Southern blot or immunoblot experiments such as polyvinylidene fluorophore, nitrocellulose, nylon and other suitable materials. Examples of suitable membranes include PVDF, Biotrans (ICN), Zeta-probe (Bio-Rad), Colony/Plaque Screen (NEN), Hybond-N (Amersham), Magnacharge (MSI), Magnagraph (MSI) and Hybond ECL (Amersham).

As used in the present invention, the term "array" refers to an ordered arrangement of elements (lectins) which are capable of interacting with proteins. The elements forming the array are preferably different and include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 different elements. The arrays preferably have a density of at least 5 points/cm$^2$, preferably at least 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000 points/cm$^2$ and, even more preferably, at least 10,000 points/cm$^2$.

Typically, the lectins forming part of the microarrays are selected based on the affinity thereof for carbohydrates expected to be in the sample. It is thus possible to use databases of the public domain to identify those lectins having the desired affinity, such as the D lectin database available at www.cermav.cnrs.fr/lectines/, the LECstar database available at www.dadamo.com/lecster2/Lecster.htm, the Lectindb database (Chandra et al., Glycobiology, 2006, 16:938-946).

Alternatively, it is possible to use different known techniques for selecting the lectins that will form part of the microarrays, such as affinity selection (panning) using cells, pseudocells, glycoproteins having a determined carbohydrate or the specific sugar. It is thus possible to select a lectin or group of lectins by affinity and to use those showing the desired affinity in the microarrays of the invention.

Another possibility for selecting the set of lectins that will form part of the microarrays for their use in the context of the present invention includes the modification of the lectin sequences of known specificity for modifying their selectivity. It is thus possible to introduce different types of mutations (insertions, deletions or point mutations) at the ligand binding site of a determined lectin for obtaining modified lectins or collections of lectins with a different degree of affinity for the ligand or with a different specificity of ligand. Alternatively, the generation of new lectins is possible by means of diversification techniques based on the recombination between the lectin encoding sequences (shuffling).

The method of the invention can be carried out using a variable number of binding reagents in each array. The invention thus contemplates the use of supports comprising at least one reagent, at least two reagents, at least 3 reagents, at least 4 reagents, at least 5 reagents, at least 6 reagents, at least 7 reagents, at least 8 reagents, at least 9 reagents, at least 10 reagents and so on and so forth.

As used in the present invention, the term "uniformly coat" refers to the microarrays distributed on the entire surface of the support or at least on the surface of the support which is contacted with the first support. The invention thus contemplates the use of second supports in which the density of microarrays is of at least around 4 arrays/cm$^2$, at least around 8 arrays/cm$^2$, at least around 16 arrays/cm$^2$, at least around 64 arrays/cm$^2$ or at least around 278 arrays/cm$^2$.

In a preferred embodiment, the support comprising the arrays of immobilized reagents and on which the transfer of the fractionated proteins is performed has been treated after the immobilization of the reagents and before the transfer with a blocking agent for the purpose of removing as much as possible the non-specific binding sites that may exist in the membrane. The blocking agents can be dispersed or dissolved in the buffer before their use. Alternatively, the use of stock solutions of said blocking agents which are prepared beforehand and which only need to be diluted in the suitable solvent or in the buffer used for the transfer immediately before their use is possible. Stock solutions of blocking reagents include solutions up to 20×, up to 10×, up to 5× or up to 2× the concentrations typically used in protein transfer processes. Blocking agents which can be used in the context of the present invention include but are not limited to total serum, fractionated serum, bovine serum albumin, casein, soy protein, low-fat milk, gelatin, fish serum, goat immunoglobulin, rabbit immunoglobulin, mouse immunoglobulin, horse immunoglobulin, human immunoglobulin, pig immunoglobulin, chicken immunoglobulin, milk serum proteins, rice proteins, alga proteins or synthetic blocking agents which can be acquired ready for their use such as WesternBreeze, I-BLOCK, BlockIt, PerfectBlock, Synthetic Blocking Buffer (BioFX Labs), Gelantis BetterBlock, SeaBlock, Starting Block and Protein-Free Blocking Buffer (Pierce).

In the event that the support on which the method of the invention is carried out is a glass slide activated as ester-NHS, the blocking of unoccupied active sites is preferably carried out with an amine for example ethanolamine or BSA or casein or skim milk or PEG.

The concentration of blocking agent in the solution used for blocking the membrane can range from between close to 0.1% by weight to close to 50% by weight, from between close to 1% by weight to close to 40% by weight, from between close to 2.5% by weight to close to 25% by weight, from between close to 5% by weight to close to 125% by weight or close to 10% by weight. Alternatively, the concentration of blocking agent in the solution used for blocking the membrane can be up to approximately 75 mg/ml, up to approximately 50 mg/ml, up to approximately 40 mg/ml, up to approximately 30 mg/ml, up to approximately 20 mg/ml, up to approximately 15 mg/ml, up to approximately 10 mg/ml, up to approximately 5 mg/ml, up to approximately 2.5 mg/ml, up to approximately 1 mg/ml, up to approximately 0.5 mg/ml, up to approximately 0.25 mg/ml or up to approximately 0.1 mg/ml.

In a third phase, the first method of the invention comprises determining the presence of proteins associated with the reagents forming the microarrays. Thus, the occurrence of a protein associated with a specific reagent in a specific array will be indicative of the presence in the sample of a protein with a molecular weight and/or isoelectric point spatially coinciding with said array between the second support of a protein having affinity for a specific reagent. Thus, given that the arrays comprise a plurality of reagents, the method of the invention allows obtaining a proteomic fingerprint of each region of molecular weight/isoelectric point in the first support.

Thus, "proteomic fingerprint" refers to the information provided by the amount of detected binding of the proteins in a region of molecular weight/isoelectric point to the different reagents forming part of the array which overlaps said region of the first support. The fingerprint can be graphically expressed by means of a histogram which reflects the relative binding intensities of the glycoprotein to each of the lectins forming part of the array.

The determination of the presence of the protein which is associated with a determined reagent within a determined microarray can be carried out using methods widely known by the person skilled in the art. These methods include but are not limited to fluorescence, radioimmunoassay and detection by means of immunolabeling.

It is thus possible to label the proteins of the samples with a fluorescent reagent before their fractionation to then detect the fluorescence emitted by said reagent which is associated with each position of the array of lectins. Nevertheless, in a preferred embodiment in the event that the proteins of the sample have been covalently modified with a first member of a binding pair, the stage of detecting the glycoproteins which have bound to the lectins of the arrays is carried out by means of contacting the support with a second member of a binding pair comprising a detectable compound.

Suitable binding pairs which can be used in the present invention include but are not limited to hapten or antigen/antibody, for example, digoxin and anti-digoxin antibodies,
biotin or biotin analogs (for example, aminobiotin, iminobiotin or desthiobiotin)/avidin or streptavidin,
sugar/lecithin,
enzyme and cofactor
folic acid/folate
double stranded oligonucleotides which selectively bind to proteins/transcription factors,
nucleic acid or nucleic acid analog/complementary nucleic acid,
receptor/ligand, for example, steroid hormone receptor/steroid hormone It will be understood that the term "first" and "second" member of a binding pair is relative and that each of the previous members can be seen as the first or second member of the binding pair.

In an even more preferred embodiment, when biotin has been used as the first member of a binding pair, the second member of the binding pair is avidin or a functionally equivalent variant thereof.

As used in the present invention, the term "avidin" refers to a glycoprotein found in egg whites and in tissues of birds, reptiles and amphibians protein and which has the capacity to bind to biotin with high affinity. The term avidin includes both avidin found naturally in the eggs of Gallus gallus (NCBI accession numbers NM_205320.1/GL45384353en) as well as the orthologues of said protein in other species.

As used in the present invention, the expression "functionally equivalent avidin variant" refers to all those polypeptides resulting from the modification of avidin by means of the substitution, addition, removal and/or chemical modification of one or more residues and which substantially maintain the biotin binding capacity with an affinity of at least $10^8$ M$^{-1}$, at least $10^9$ M$^{-1}$, at least $10^{10}$ M$^{-1}$, at least $10^{12}$ M$^{-1}$ or at least $10^{14}$ M$^{-1}$. Illustrative and non-limiting examples of functionally equivalent avidin variants suitable for their use in the present invention include:

Avidin homologues having at least 70%, at least 80%, at least 90%, at least 95%, at least 96%, at least 97%, at least 98%, at least 99% amino acid sequence identity with respect to avidin as found in nature.
Fragments of avidin such as those described by Hiller et al. (Biochem J., 1991, 278: 573-85).
Variants resulting from the chemical modification of avidin such as those resulting from the complete or partial modification of glycosylation and fragments thereof as well as the completely deglycosylated avidin variant known as neutravidin.
Streptavidin, corresponding to the protein from Streptomyces avidinii (accession number CAA00084.1 in GenBank), as well as the orthologues, homologues and fragments of streptavidin defined in the same manner as avidin. Streptavidin comprises 4 subunits each of which contains a binding site for biotin.
Avidin mutants such as those described in WO05047317A1
Avidin-like proteins described in WO06045891,
The recombinant avidin described in WO0198349,
The avidin variants described in WO0027814,
The monomeric streptavidin described in WO06084388,
The modified streptavidin dimmers described in WO06058226,
The protein with biotin binding capacity described in WO04018509,
The streptavidin having a higher affinity for biotin described in WO9840396,
The modified streptavidin and avidin molecules described in WO9640761,
The streptavidin mutants described in WO9711183,
The streptavidin with modified affinity described in WO9624606.

Different avidin variants are commercially available, such as Extravidin (Sigma-Aldrich), NeutrAvidin (Thermo Scientific), NeutrAvidin (Invitrogen) and NeutraLite (Belovo).

In a preferred embodiment, when the proteins object of study in the method of the invention are labeled with biotin, the detection of the proteins associated with the different cells of the arrays is carried out with neutravidin, since avidin is a glycosylated protein which can be associated with lectins the binding sites of which have not been saturated with the proteins of the mixture, thus resulting in false positives.

The term "detectable compound" is used in the present invention to refer to any compound which can be detected either directly due to any property of said compound or indirectly because said compound has the capacity to modify a second molecule which is detectable. The compound can be a fluorescent group, a group luminescent or an enzyme. If the detectable compound is an enzyme, then this enzyme must be capable of generating a detectable signal, for example, after adding an activator, substrate, amplifying agent and the like. The enzymes which are suitable as detectable tags for the present invention and the corresponding substrates include:

|Alkaline phosphatase:
  Chromogenic substrates: substrates based on p-nitrophenyl phosphate (p-NPP), 5-bromo-4-chloro-3-indolyl phosphate/nitroblue tetrazolium (BCIP/NBT), Fast-Red/naphthol phosphate-AS-TS
  Fluorogenic substrates: 4-methylumbelliferyl phosphate (4-M U P), 2-(5'-chloro-2'-phosphoryloxyphenyl)-6-chloro-4-(3H)-quinazolinone (CPPCQ), 3,6-fluorescein diphosphate (3,6-FDP), diazonium salts of Fast Blue BB, Fast Red TR, or Fast Red Violet LB.
|Peroxidases:
  Chromogenic substrates based on 2,2-azinobis(3-ethylbenzothiazoline-6-sulfonic) acid (ABTS), o-phenylenediamine (OPT), 3,3',5,5'-tetramethylbenzidine (TMB), o-dianisidine, 5-aminosalicylic acid, 3-dimethylaminobenzoic acid (DMAB) and 3-methyl-2-benzothiazolinehydrazone (MBTH), 3-amino-9-ethylcarbazole (AEC) and 3,3'-diaminobenzidine (DAB) tetrahydrochloride.
  Fluorogenic substrates: 4-hydroxy-3-methoxyphenylacetic acid, reduced phenoxazines, reduced benzothiazines, including Amplex® Red reagent, Amplex UltraRed reagent and reduced dihydroxanthenes.
|Glycosidases:
  Chromogenic substrates: o-nitrophenyl-β-D-galactoside O—NPG), p-nitrophenyl-β-D-galactoside and 4-methylumbelliphenyl-β-D-galactoside (MUG) for β-D-galactosidase.
  Fluorogenic substrates: resorufin β-D-galactopyranoside, fluorescein digalactoside (FDG), fluorescein diglucuronide, 4-methylumbelliphenyl-β-D-galactopyranoside, carboxyumbelliferyl-β-D-galactopyranoside and fluorinated coumarin β-D-galactopyranosides.

[Oxidoreductases (luciferase):
Luminescent substrates: luciferin.

In an even more preferred embodiment, the detectable compound which is bound to the second member of the binding pair is a fluorescent compound. As used in the present invention, the term "fluorescent compound" refers to all those compounds which absorb light at a determined wavelength or wavelength range and emit light at a different wavelength or wavelength range. Fluorescent compounds suitable for their use in the present invention include but are not limited to ethidium bromide, SYBR Green, fluorescein isothiocyanate (FITC), tetramethyl rhodamine isothiol (TRIT), 5-carboxyfluorescein, 6-carboxyfluorescein, fluorescein, HEX (6-carboxy-2',4,4',5',7,7'-hexachlorofluorescein), Oregon Green 488, Oregon Green 500, Oregon Green 514, Joe (6-carboxy-4',5'-dichloro-2',7'-dimethoxyfluorescein), 5-carboxy-2',4', 5',7'-tetrachlorofluorescein, 5-carboxyrhodamine, rhodamine, tetramethylrhodamine (Tamra), Rox (carboxy-X-rhodamine), R6G (rhodamine 6G), phthalocyanines, azomethines, cyanines (Cy2, Cy3 and Cy5), Texas Red, Princeton Red, BODIPY FL-Br2, BODIPY 530/550, BODIPY TMR, BODIPY 558/568, BODIPY 564/570, BODIPY 576/589, BODIPY 581/591, BODIPY TR, BODIPY 630/650, BODIPY 650/665, DABCYL, Eosin, Erythrosine, ethidium bromide, green fluorescent protein (GFP) and the analogs thereof, inorganic fluorescent labels based on semiconductor nanocrystals (Quantum dot), fluorescent labels based on lanthanides such as $Eu^{3+}$ and $Sm^{3+}$ and the like.

The third stage is typically carried out using a solution comprising an agent showing affinity for the glycoproteins in a physiologically acceptable aqueous solution. The buffer in which the incubation of the membranes with the agent with affinity for the glycoproteins is performed can have a pH from between close to 4 up to close to 9, from between close to 5 up to close to 8, from between close to 6 up to close to 7.5 and contains at least one buffering agent of the type of phosphate, bicarbonate, TAPS, Bicine, Tris, Bis-Tris, Tricine, HEPES, TES, MOPS, PIPES, Cacodylate, MES, acetate, ADA, ACES, cholamine, BES, acetamidoglycine or glycinide buffer. Buffers suitable for their use as diluents include but are not limited to PBS, Hank solution, TBS, TE, TEN or the like. The diluent can optionally contain a detergent such as for example a non-ionic, non-denaturing detergent of the type of Triton X-100, Triton X-114, NP-40, Brij-35, Brij 58, Tween-20, Tween-80, octylglucoside and octylthioglucoside.

In the event that the membrane (or slide) has been contacted with a blocking agent, the inclusion of said blocking agent in the solution or solutions which are used for detecting the presence of the glycoproteins associated with the immobilized lectins is possible. Thus, in the event that the glycoproteins have been biotinylated, the stage of incubating with avidin or the labeled variant thereof is carried out in a buffer solution comprising variable amounts of the blocking agent.

In another aspect, the invention contemplates the possibility of adding to each of the lectins forming each of the cells of the microarray a small amount of a protein labeled with a detectable group, typically a fluorophore, said protein being a protein which is not expected to specifically interact with the proteins present in the sample and said fluorophore being a fluorophore compatible with the one that is used for detecting the positions in the microarrays in which first members of a binding pair are associated.

Proteins suitable for said labeling of the individual cells of each array include but are not limited to bovine serum albumin, mouse serum albumin, ovalbumin, hemocyanin and the like.

Compatible fluorophores include all those in which the excitation/emission maxima take place at wavelength ranges which do not overlap one another and include but are not limited to rhodamine and fluorescein isothiocyanate (FITC), tetramethyl rhodamine isothiocyanate (TRITC) and fluorescein isothiocyanate (FITC), tetramethylrhodamine (TAMRA) and FITC or FITC-dextran or fluorescein and eosin.

In a preferred embodiment, the proteins of the sample the affinity of which for a determined reagent is to be studied are glycoproteins and the reagent or reagents forming part of the microarrays are selected from the group of a lectin and an anti-glycan antibody.

In another embodiment, a pattern of glycoproteins is detected in the microarrays, said pattern of glycoproteins being indicative of the carbohydrate content of the glycoprotein coinciding spatially with said microarray.

Thus, in another aspect the invention relates to a method for analyzing the carbohydrate content of the glycoproteins of a protein sample which comprises
(a) fractionating the proteins present in the sample in a first support,
(b) transferring the fractionated proteins from said first support to a second support, wherein said second support is uniformly coated by a set of microarrays of immobilized lectins, wherein each microarray of lectins comprises at least one lectin of known specificity, wherein the transfer is carried out under conditions suitable for maintaining in the second support the two-dimensional organization of the proteins of the first support and for causing the interaction between the glycoproteins which are transferred and the lectins of the arrays coinciding spatially with said glycoproteins and
(c) visualizing the presence of glycoproteins at the different points forming the microarrays coinciding spatially in the support with the proteins transferred wherein the pattern of proteins which is detected in the arrays is indicative of the carbohydrate content of the protein coinciding spatially with said array.

The method of the invention can be carried out using a variable number of lectins in each array. The invention thus contemplates the use of supports comprising at least one lectin, at least two lectins, at least 3 lectins, at least 4 lectins, at least 5, at least 6, at least 7, at least 8, at least 9, at least 10 lectins and so on and so forth.

The determination of the presence of the glycoprotein which is associated with a lectin within a determined array can be carried out using methods widely known by the person skilled in the art. These methods include but are not limited to fluorescence, radioimmunoassay and detection by means of immunolabeling.

Putting the method of the invention into practice using arrays formed by lectins allows obtaining a "glycomic fingerprint", in which said term refers to the information provided by the detected level of binding of the glycoproteins in a region of molecular weight/isoelectric point to the different lectins forming part of the array which overlaps said region of the first support. The fingerprint can be graphically expressed by means of a histogram which reflects the relative binding intensities of the glycoprotein to each of the lectins forming part of the array.

The method of the invention is particularly useful for the diagnosis or identification of physiological situations and of diseases in which an alteration in the pattern of glycosylation of one or more proteins occurs. It is therefore possible to analyze a sample from a patient and conclude if said patient suffers a determined disease by means of detecting differences in the pattern of glycosylation of the glycoproteins of the sample compared to a control patient. It is thus known that there are alterations in the pattern of glycosylation of proteins in I-cell disease, in the set of disorders generically known as "congenital alterations of glycosylation", including type I disorders, in which the assembly of the glycoprotein is altered, and in type II disorders in which there is a cytosolic phosphomannomutase activity deficiency, in leukocyte adhesion deficiency type II, in hereditary erythroblastic multinuclearity with a positive acidified serum test (HEMPAS), also known as congenital dyserythropoietic anemia type II, Wiskott-Aldrich syndrome as well as diseases characterized by the deficiency of one or several lysosomal glycosidases, generically known as "glycoproteinosis" and which, depending on the glycosidase that is deficient, are characterized by the accumulation and urinary secretion of one type of oligosaccharide or another. Cases have been described of glycoproteinosis characterized by Sialidase, β-Galactosidase, β-Hexosaminidase B, α-Fucosidase, N-Aspartyl-β-glucosaminidase and α-Mannosidase deficiency. There are also different acquired diseases in which an alteration of the pattern of glycosylation of different glycoproteins occurs (see Sedand and Seta, 2000, Clinical Chemistry, Clinical Chemistry 46:795-805).

The method of the invention is useful for determining the pattern of glycosylation of proteins obtained in a recombinant manner since it is known that the glycosylation of a glycoprotein can be affected by different factors during the production in the bioreactor, such as pH, partial oxygen pressure (Kunkel, J. P., et al., 2000, Biotechnol. Prog. 16, 462-70; Zhang, F., et al., 2002, Biotechnol. Bioeng. 77, 219-24; Senger, R. S., Karim, M. N., 2003, Biotechnol. Prog. 19:1199-209; Muthing, J., et al., 2003, Biotechnol. Bioeng. 83:321-34). The possibility of rapidly analyzing the pattern of glycosylation of a glycoprotein obtained in a bioreactor allows adjusting the culture conditions such that the desired glycosylation is reached.

Method for the Identification of a Reagent Showing Affinity for a Determined Protein The method of the invention can be carried out using a starting sample comprising a single protein or a substantially pure protein. Thus, it would be possible to identify out of a collection of reagents those which specifically interact with said protein. To that end, the sample used in stage (i) would comprise a substantially pure protein and the microarray used in stage (ii) would be formed by a plurality of reagents the affinity of which for said protein is to be assayed. This usefulness is of particular interest in the event that there is available of a collection of antibodies directed against a protein, since it would allow rapidly determining which antibodies, out of all those present in said collection, show higher affinity for the determined protein.

Therefore, in a second aspect the invention relates to a method (hereinafter second method of the invention) for the identification in a mixture of reagents of a reagent showing affinity for a target protein which comprises (i) fractionating said target protein based on at least one physicochemical property of said protein, (ii) transferring the target protein from said first support to a second support, wherein said second support is uniformly coated by a set of microarrays, wherein each microarray comprises a plurality of reagents from which the presence of a reagent with the capacity to bind specifically to said target protein is to be identified and wherein said plurality of reagents is immobilized in said second support, wherein the transfer is carried out under conditions suitable for maintaining in the second support the two-dimensional organization of the fractionated proteins in the first support and for causing the interaction between the target protein which is transferred and the reagent coinciding spatially in the second support with said protein and (iii) detecting the presence of the target protein associated with said immobilized reagents wherein the presence of a target protein associated with one or several of the reagents is indicative of the presence in the mixture of reagents of at least one reagent which shows the capacity to bind specifically to the target protein.

The second method of the invention is essentially carried out as described in relation to the first method of the invention such that the terms and expressions defined in the context of the first method are also applied for the second method.

In a preferred embodiment, the plurality of reagents is antibodies from which it is to be determined if there is an antibody which shows affinity for a determined target protein. In this application, the different antibodies which are to be studied are immobilized in microarrays uniformly on the entire support and the target protein is incorporated in a first support based on its physicochemical properties. Subsequently, after transferring the protein to the second support, the presence of the protein in one or several cells of the microarrays located in the region of the second support which corresponds to the region of the first support in which the target protein is located is detected. Since it is known which antibody has been applied in which cell of the microarrays, it is possible to conclude which of the antibodies forming the array are capable of binding specifically to the target protein.

Method for the Identification of a Cell Glycosylation Modulator Compound

In another aspect, the invention relates to a method (hereinafter second method of the invention or screening method of the invention) for the identification of a cell glycosylation modulator compound which comprises (i) contacting a cell population with the candidate compound, (ii) obtaining a preparation of proteins of said cell population, (iii) fractionating the proteins present in said sample in a first support, (iv) transferring the fractionated proteins from said first support to a second support, wherein said second support is uniformly coated by a set of microarrays of immobilized lectins, wherein each microarray of lectins comprises at least two different lectins of known specificity, wherein the transfer is carried out under conditions suitable for maintaining in the second support the two-dimensional organization of the proteins of the first support and for causing the interaction between the glycoproteins which are transferred and the lectins of the arrays coinciding spatially with said glycoproteins and (v) visualizing the presence of glycoproteins at the different points forming the microarrays coinciding spatially in the support with the transferred proteins wherein an alteration in the pattern of glycoproteins of the sample obtained from the cell population treated with the candidate compound in relation to a sample of proteins obtained from a cell population which has not been treated with said compound is indicative of the compound being a cell glycosylation modulator.

In a first stage, the second method of the invention contemplates contacting the cells with a candidate compound. "Contacting" a cell with the candidate compound is understood, according to the present invention, as any possible way of introducing the candidate compound into the cell with glycosylating activity. Thus, in the event that the candidate compound is a low molecular weight molecule, it is sufficient to add said molecule to the culture medium. In the event that the candidate compound is a high molecular weight molecule (for example, biological polymers such as a nucleic acid or a protein), it is necessary to provide the means so that this molecule can access the inside of the cell. In the event that the candidate molecule is a nucleic acid, conventional transfection methods can be used, as has been described above for introducing the DNA construct. In the event that the candidate compound is a protein, the cell can be contacted both with the protein directly and with the nucleic acid encoding it coupled to elements which allow its transcription/translation once they are inside the cell. To that end, any of the aforementioned methods can be used to allow their entrance inside the cell. Alternatively, it is possible to contact the cell with a variant of the protein to be studied which has been modified with a peptide that is capable of promoting the translocation of the protein inside the cell, such as the Tat peptide derived from the HIV-1 TAT protein, the third helix of the homeodomain of the of *D. melanogaster* Antennapedia protein, the herpes simplex virus VP22 protein and arginine oligomers (Lindgren, A. et al., 2000, *Trends Pharmacol. Sci*, 21:99-103, Schwarze, S. R. et al., 2000, *Trends Pharmacol. Sci.*, 21:45-48, Lundberg, M et al., 2003, *Mol. Therapy.* 8:143-150 and Snyder, E. L. and Dowdy, S.F., 2004, *Pharm. Res.* 21:389-393).

In a preferred embodiment, the method of identifying compounds involves assaying a combinatorial modulator compound library. A combinatorial chemical library can be a collection of several chemical compounds generated by chemical or biological synthesis or synthesis by means of combining a number of reactive chemical building blocks. For example, a linear combinatorial chemical library, such as a polypeptide library, is obtained by means of combining a set of chemical components (amino acids) in all the possible forms for a determined compound length (for example, the number of amino acids in a polypeptide). Libraries formed by millions of chemical compounds can thus be obtained. Alternatively, there are a number of compound libraries which are commercially available, both of compounds obtained by synthesis from building blocks and of natural compounds obtained from bacteria, fungi, plants and animal extracts.

Libraries suitable for their use in the methods of identification of the present invention include but are not limited to peptide libraries (see, for example, U.S. Pat. No. 5,010,175; Furka, Int. J. Pept. Prot. Res., 37:487-493, 1991; Houghton et al., Nature, 354:84-88, 1991; WO91/19735; Lam et al., Nature, 354:82-84, 1991; ef Houghten alfa /., Naturaleza, 354:84-86, 1991), combinatorial libraries formed by D and/or L-amino acids, phosphopeptide libraries (Songyang ef al, Cell, 72:767-778, 1993), antibody libraries (including but not limited to polyclonal antibodies, monoclonal antibodies, humanized antibodies, anti-idiotypic antibodies, chimeric or single-chain antibodies, and Fab, F(ab')$_2$ and Fab), libraries of small organic or inorganic molecules, random bio-oligomer (WO92/00091), benzodiazepine (for example, U.S. Pat. No. 5,288,514), diversomer (Hobbs et al., Proc. Natl. Acad. Sa. U.S.A., 90:6909-6913, 1993), vinylogous polypeptide (al Hagihara et al., Am. J. Chem. Soc, 114:6568, 1992), non-peptide peptidomimetics with glucose scaffold (Hirschmann et al., J. Am. Chem. Soc, 114:9217-9218, 1992), oligocarbamates (Cho et al., Science, 261:1303, 1003), and/or peptidyl phosphonates (Campbell et al., J. Org. Chem., 59:658, 1994), nucleic acid libraries (Sambrook et al. Molecular Cloning, A Laboratory Manual, Cold Springs Harbor Press, NY., 1989; Ausubel et al., Current Protocols in Molecular Biology, Green Publishing Associates and Wiley Interscience, N.Y., 1989), peptide nucleic acid libraries (U.S. Pat. No. 5,539,083), antibody libraries (Vaughn et al., 1996, Nat. Biotechnol, 14:309-314), carbohydrate libraries (Liang et al., Science, 274:1520-1522, 1996; U.S. Pat. No. 5,593,853), libraries of small organic molecules, such as benzodiazepines, isoprenoids, thiazolidinones and metathiazones, pyrrolidines and the like.

The libraries can include a variable number of compounds (members). The compound libraries can thus contain at least about 100 members, at least up to about 1000 members, at least up to about 5000 members, at least up to about 10,000 members, at least up to about 100,000 members or at least up to about 500,000 members or even more than 500,000 members.

Preferably, the compound to be assayed is not isolated, but rather forms part of a more or less complex mixture that is either derived from a natural source or forming part of a compound library. Examples of compound libraries which can be assayed according to the method of the present invention include but are not limited to libraries of peptides including both peptides and peptide analogs comprising D-amino acids or peptides comprising non-peptide bonds, libraries of nucleic acids including nucleic acids with non-phosphodiester bonds of the phosphorothioate type or peptide nucleic acids, libraries of antibodies, of carbohydrates, of low molecular weight compounds, preferably of organic molecules, of peptidomimetics, and the like. In the event that a library of low molecular weight organic compounds is used, the library could have been preselected in order to contain compounds which can more easily access the inside of the cell. The compounds can thus be selected based on determined parameters such as size, lipophilicity, hydrophilicity, capacity to form hydrogen bridges.

Alternatively, the compounds to be assayed can form part of an extract obtained from a natural source. The natural source can be animal, plant obtained from any environment, including but not limited to extracts from land, air, marine organisms and the like.

The cells which can be used in stage (a) are not particularly limiting of the scope of the invention provided that they are cells capable of performing post-translational modification of proteins by means of adding N-glycan residues, i.e., eukaryotic cells. The eukaryotic cells can be of any organism but yeast, plant or mammal cells are preferred. The type of cell will essentially depend on the type of glycosylation to be studied. Thus, mammal cells are used when compounds modulating complex glycosylation are to be identified. Illustrative and non-limiting examples of mammal cells which can be used in the screening method of the present invention include but are not limited to hamster ovary (CHO) cells such as CHO-Kl (ATCC CCL-61), DG44 (Chasin et al., 1986, Som. Cell Molec. Genet., 12:555-556; and Kolkekar et al., 1997, Biochemistry, 36:10901-10909), CHO-Kl Tet-On (Clontech), CHO designated ECACC 85050302 (CAMR, Salisbury, Wiltshire, UK), CHO clone 13 (GEIMG, Genova, IT), CHO clone B (GEIMG, Genova, IT), CHO-Kl/SF designated ECACC 93061607 (CAMR, Salisbury, Wiltshire, UK), RR-CHOKl designated ECACC 92052129 (CAMR, Salisbury, Wiltshire, UK), CHO cells negative for dihydrofolate reductase (CHO/-DHFR, Urlaub and Chasin, 1980, Proc. Natl. Acad. Sci. USA, 77:4216), SV40-transformed monkey kidney CVl cells (COS, COS-7, ATCC CRL-1651 cells); human embryonic kidney cells (293, 293T cells); baby hamster kidney cells (BHK, ATCC CCL-IO); monkey kidney cells (CVl, ATCC CCL-70); African Green Monkey kidney cells (VERO-76, ATCC CRL-1587; VERO, ATCC CCL-81); mouse Sertoli cells (TM4, Mather, 1980, Biol. Reprod., 23:243-251); human cervical carcinoma cells (HELA, ATCC CCL-2); dog kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, Annals NY Acad. Sci., 383:44-68); MCR 5 cells; FS4 cells.

Other cells of a non-mammal origin which can be used in the present invention include Sf9 cells and other cells which can be used in baculovirus-based expression systems (Jarvis, Virology Volume 310, Issue 1, 25 May 2003, Pages 1-7), plant cells such as tobacco cells, tomato cells, corn cells, alga cells, or yeast cells, such as from *Saccharomyces* sp. (for example *Saccharomyces cerevisiae*), *Hansenula* sp. (for example *Hansenula polymorpha*), *Yarrowia* sp. (for example *Yarrowia lipolytica*) or *Pichia* sp. (for example *Pichia pastoris*).

The cells which are used in the screening method of the invention can be cells in culture, or they can alternatively form part of an organism (for example, an animal, a plant which may or may not be transgenic). In the case of transgenic animals or plants, it is possible to use modified plants expressing an enzyme involved in glycosylation.

In a second stage, the second method of the invention comprises obtaining a preparation of proteins of said cell population. The proteins can be obtained from the cells by means of methods known by the person skilled in the art which require separating the cells from the culture medium by any method known by persons skilled in the art (trypsinization and centrifugation or filtration) and the rupture of said cells in an inert solution (freezing/thawing cycles, homogenization, sonication, cavitation, use of detergents and the like).

Once the preparation of proteins has been obtained from the cell treated with the candidate compound, the second method of the invention contemplates a third stage (fractionating the proteins present in said sample in a first support), a fourth stage (transferring the fractionated proteins from said first support to a second support) and a fifth stage (visualizing the glycoproteins at the different points forming the microarrays) which are essentially carried out in the same manner as the second, third and fourth stages of the first method of the invention. Therefore, the definitions of the terms used in the context of the first method of the invention are also applied for the second method of the invention.

As in the first method of the invention, it is possible to pre-treat the support containing the immobilized lectins with a blocking agent before performing the transfer such that the non-specific binding sites in the support containing the lectins are removed. Suitable blocking agents have been described in detail in the context of the first method of the invention.

The compounds identified by means of the methods described in the method of the invention can be used as "guide compounds" for subsequently obtaining compounds with greater activity by means of refining their structure or they can be used directly as cell glycosylation modulating agents.

The method of identifying compounds of the invention can be carried out in parallel with different types of controls which allows increasing the reliability of the results obtained. Thus, the method can be carried out together with a negative control, wherein the method is put into practice using a compound which does not affect the processes of glycosylation or with the carrier in which the candidate compound is located. Positive controls can alternatively be used, wherein the method is carried out in the presence of compounds the capacity of which to modulate cell glycosylation is known. Compounds suitable for their use as a positive control include but are not limited to tunicamycin A, castanospermine, swainsonine, deoxynojirimycin, benzyl-O—N-acetyl-D-galactosamine and derivatives thereof such as those described by Patsos et al. (Biochemical Society Transactions, 2005, 33:4) Method for the Characterization of the Specificity of an Enzyme Capable of Modifying the Glycans of a Glycoprotein The method of the present invention is useful for characterizing the activity of an enzyme which is capable of modifying the glycans of a glycoprotein by means of contacting a determined glycoprotein or a mixture of glycoproteins with the enzyme to be studied followed by the determination of the binding pattern of the glycoprotein before and after the treatment with the enzyme. If differences between the profile of binding to the pattern of lectins are observed after the treatment with the enzyme, it is indicative of the enzyme being capable of acting on the glycans of the glycoprotein. Additionally, the determination of the lectins to which the glycoprotein binds after the treatment with the enzyme allows identifying which type of modification the glycan has undergone and thus know the specificity of the enzyme.

Thus, in another aspect the invention relates to a method for the characterization of the specificity of an enzyme capable of modifying the glycans of a glycoprotein which comprises
  (i) contacting a preparation of glycoproteins with said enzyme under conditions suitable for said enzyme to exert its activity on the glycans forming part of the glycoproteins,
  (ii) fractionating the glycoproteins obtained in stage (a) in a first support using at least one physicochemical property of said glycoproteins,
  (iii) transferring the fractionated proteins from said first support to a second support, wherein said second support is uniformly coated by a set of microarrays of immobilized lectins, wherein each microarray of lectins comprises at least two lectins of known specificity, wherein the transfer is carried out under conditions suitable for maintaining in the second support the two-dimensional organization of the proteins of the first support and for causing the interaction between the glycoproteins which are transferred and the lectins of the arrays coinciding spatially with said glycoproteins and
  (iv) visualizing the presence of glycoproteins at the different points forming the microarrays coinciding spatially in the support with the transferred proteins and
  (v) determining the specificity of the enzyme based on the alteration of the pattern of glycoproteins of the sample treated with the glycosidase in relation to a sample of glycoproteins not treated with the glycosidase.

As used in the present invention, the term "enzyme capable of modifying the glycans of a glycoprotein" refers to any protein which is capable of acting on and modifying specifically the glycans forming part of a glycoprotein, either by means of adding new sugar residues to the pre-existing glycans or by means of removing one or several sugar residues from the glycan. The invention also contemplates the possibility of studying both enzymes that act specifically on the glycans associated with the protein through the lysine side chains (N glycans) and those that act specifically on the glycans associated with the proteins through the serine/threonine side chains (O glycans). Thus, enzymes which can be studied by means of the method of the present invention include both glycosidases and glycosyltransferases.

Thus, enzymes the activity of which can be studied by means of the method described in the present invention include but are not limited to hexosyltranfereses, glycoprotein β-galactosyltransferase, glycoprotein 6-α-L-fucosyltransferase, dolichol phosphate mannose transferase, α-1,3-mannosyl glycoprotein 2-β-N-acetylglucosaminyl transferase, dolichyl phosphate β-glucosyltransferase, oligomannosyltransferase, oligomannosyl synthase, 3-α-mannosyltransferase glycolipid, N,N'-diacetylchitobiosyl pyrophosphoryl dolichol β-mannosyltransferase, α-1,6-mannosyl-glycoprotein 2-β-N-acetylglucosaminyl transferase, β-1,4-mannosyl-glycoprotein-4-β-N-acetylglucosaminyl transferase, α-1,3-mannosyl-glycoprotein 4-β-N-acetylglucosaminyl transferase, α-1,6-mannosyl-glycoprotein 6-β-N-acetylglucosaminyl transferase, β-1,6-mannosyl-glycoprotein-4-β-N-acetylglucosaminyl transferase, β-galactosidase α-2,6-sialyltransferase, mannosyl-oligosaccharide glucosidase, mannosyl-oligosaccharide 1,2-α-mannosidase, mannosyl-oligosaccharide 1,3-1,6-α-mannosidase, endoglycosidase H (Endo H), Endo F, N-Glycanase F (PNGase F), as well as exo- and endoglycosidases such as α-galactosidase, β-Galactosidase, N-acetylhexosaminidase, α-mannosidase, β-mannosidase, α-fucosidase.

Method for the Determination of the Presence of a Determined Sugar Residue in Terminal Position in the Oligosaccharide Chains of a Preparation of Glycoproteins In another aspect, the invention relates to a method (hereinafter third method of the invention) for the determination of the presence of a sugar residue in terminal position in the glycans of the glycoproteins of a protein preparation which comprises
  (i) fractionating the proteins present in said preparation in a first support,
  (ii) transferring the fractionated proteins from said first support to a second support, wherein said second support is uniformly coated by a set of microarrays of immobilized lectins, wherein each microarray of lectins comprises at least two different lectins of known specificity, and wherein at least one of said lectins is capable of binding specifically to glycoproteins having said sugar in terminal position of the glycans of said glycoproteins, wherein the transfer is carried out under conditions suitable for maintaining in the second support the two-dimensional organization of the proteins of the first support and for causing the interaction between the glycoproteins which are transferred and the lectins of the arrays coinciding spatially with said glycoproteins and wherein the transfer is carried out in presence of said sugar and
  (iii) visualizing the presence of glycoproteins at the different points forming the microarrays coinciding spatially in the support with the transferred proteins
wherein an alteration in the pattern of glycoproteins of the sample obtained in presence of the sugar with respect to the pattern of glycoproteins obtained when the stage (b) has been carried out in absence of said sugar is indicative of the presence of residues of said sugar in terminal position in the glycans of the glycoproteins. The third method of the invention is essentially carried out in the same manner as the first method of the invention with the exception that the stage of transferring the fractionated proteins to the support containing the arrays of lectin (stage (b)) is carried out in the presence of monomers of the sugar the presence of which in the N-glycans of the glycoprotein or of the mixture of glycoproteins is to be studied. Thus, if the sugar is the same as the one occurring in the N-glycans, the latter will compete with the N-glycan for binding to the corresponding lectin, which translates into a reduction of the amount of glycoprotein associated with the lectin compared to that observed when the transfer is carried out in the absence of said molecule. It is thus possible to identify if a determined sugar is in a determined glycoprotein or in a mixture of glycoproteins.

The first stage of the third method of the invention comprises fractionating the proteins present in said preparation in a first support. This stage is essentially carried out as described above in the context of the first and second method of the invention.

In a second stage, the fractionated proteins in the first support are transferred to a second support, wherein said second support is uniformly coated by a set of microarrays of immobilized lectins, wherein each microarray of lectins comprises at least two lectins of known specificity, and wherein at least one of said lectins is capable of binding specifically to glycoproteins having said sugar in terminal position of the glycans of said glycoproteins, wherein the transfer is carried out under conditions suitable for maintaining in the second support the two-dimensional organization of the proteins of the first support and for causing the interaction between the glycoproteins which are transferred and the lectins of the arrays coinciding spatially with said glycoproteins. This stage is essentially carried out as described above in the context of the first and second method of the invention but it is carried out in the presence of the sugar the presence of which in the glycans of the glycoproteins of the sample is to be evaluated. To do so, it is possible to add to the transfer buffer in which the transfer is performed a sufficient concentration of said sugar which inhibits by competition the binding of the glycoproteins containing said sugar to the complementary lectin.

As in the first and second methods of the invention, it is possible to pre-treat the support containing the immobilized lectins with a blocking agent before performing the transfer such that the non-specific binding sites in the support containing the lectins are removed. Suitable blocking agents have been described in detail in the context of the first method of the invention.

In a third stage, the third method of the invention comprises visualizing the glycoproteins associated with the lectins forming the microarrays. The visualization is carried out in the same manner as described above for the first method of the invention. Basically, the glycoproteins may have been labeled before their fractionation with a fluorescent reagent, which allows the direct visualization of the glycoproteins which are associated with the lectins. Alternatively, it is possible to detect the glycoproteins indirectly if they have been labeled before their fractionation with a first member of a binding pair, using for that purpose a second member of a binding pair coupled to a detectable compound.

The alteration in the pattern of glycoproteins of the sample obtained in the presence of the sugar with respect to the pattern of glycoproteins obtained when stage (b) has been carried out in the absence of said sugar is indicative of the presence of residues of said sugar in the glycans of the glycoproteins.

The possibility of determining the type of glycosylation occurring in a determined protein is useful, for example, for rapidly characterizing different glycoforms of a recombinant protein. This application is particularly relevant in the case of glycoproteins which are going to be used in therapy because it allows the comparison with the glycosylation occurring in the same protein in the organism to which the protein will be administered. Therefore, by selecting the glycoforms that are most similar to those occurring naturally, compatibility with the immune system could be increased.

The invention is now described by means of the following examples which have a merely illustrative character and which in no case limit the scope of the invention.

EXAMPLES

1. Microarrays of Lectins in Different Supports
Nitrocellulose Membranes:

The lectins Concanavalin A (ConA), Wheat germ, agglutinin (WGA), *Ricinus communis* agglutinin (RCA), *Sambucus nigra* lectin (SNA), *Griffonia* (Bandeiraea) *simplicifolia* lectin II (BSL-II), *Pisum sativum* agglutinin (PSA) and *Ulex europaeous* agglutinin I (UEA-I) obtained from Vector laboratories, Burlingame, USA and Sigma-Aldrich, were reconstituted as 1 mg/mL solutions, they were diluted 1:2. 2.8 nL of these dilutions were dispensed in the nitrocellulose membrane (BioTrace NT, Pall Life Science, East Hills, N.Y., USA) with a non-contact piezo-array dot dispenser. The membranes with the arrays of lectin were left at room temperature overnight so that they dried completely and the membranes were subsequently blocked overnight at 25° C. in PBS (phosphate-buffered saline) with 0.5% Tween-20 supplemented with 0.5% bovine serum albumin (BSA). After another washing step (washing solution: 0.5% Tween-20 in phosphate-buffered saline, PBS), the membranes which contained the microarrays were ready to perform the transfer step.

Polyvinyl Fluoride Membranes:

The PVDF membranes (Immun-Blot™ PVDF membrane, BioRad) were wetted by immersion in MeOH (1 min) and subsequently in PBS before dispensing the proteins. The lectins (1 mg/mL) were diluted 1:2 and 2.8 mL of these dilutions were applied in the PVDF membrane with a non-contact piezo-array dot dispenser. The membranes with the arrays of lectin were left at room temperature overnight so that they dried completely and the membranes were subsequently blocked overnight at 25° C. in PBS (phosphate-buffered saline) with 0.5% Tween-20 supplemented with 0.5% bovine serum albumin (BSA). After another washing step (washing solution: 0.5% Tween-20 in phosphate-buffered saline, PBS), the membranes which contained the microarrays were ready to perform the transfer step.

Glass Slides Coated by a Hydrogel Functionalized with N-Hydroxysuccinimide Esters/Slides Coated with Nitrocellulose.

The lectins Concanavalin A (ConA), Wheat germ agglutinin (WGA), *Ricinus communis* agglutinin (RCA), *Erythrina cristagalli* agglutinin (ECA), *Sambucus nigra* lectin (SNA), *Griffonia* (Bandeiraea) *simplicifolia* lectin II (BSL-II), *Pisum sativum* agglutinin (PSA), *Ulex europaeous* agglutinin I (UEA-I), *Griffonia* (Bandeiraea) *simplicifolia* lectin I (BSL-I), *Maackia amurensis* lectin I (MAL-I), *Maackia amurensis* lectin II (MAL-II), *Aleuria aurantia* lectin (AAL), *Lens culinaris* agglutinin (LCA), *Vicia villosa* lectin (VVL), Jacalin (JAC) and *Bauhinia purpurea* lectin (BPL) obtained from Vector laboratories, Burlingame, USA and Sigma-Aldrich, were reconstituted as 1 mg/mL solutions, containing 0.01% BSA conjugated with cy3 (BSA labeled with the Hilyte Plus™ 555 labeling kit, a cy3 analog, from AnaSpec, Freemont, USA). 0.7 mL of these dilutions were applied on the glass slides coated with a hydrogel polyfunctionalized with N-hydroxysuccinimide esters (Nexterion®H, Schott AG, Mainz, Germany) or on the slides coated with nitrocellulose (Nexterion®NC, Schott AG, Mainz, Germany) with a non-contact piezo-array dot dispenser. The lectins were dispensed in 4 replicas with a 0.3 mm spacing between spots in the form of subarrays (8×8) and in multiple arrays (7×22), completely covering the surface of the slide. The slides containing the microarrays of lectins were incubated at 25° C. and 75% humidity for 1 h in the case of the slides coated with functionalized hydrogel and for 24 h in the case of the nitrocellulose slides. The hydrogel slides were treated with a 50 mM ethanolamine solution in borate buffer (50 mM, pH 9.0) for 1 h to derivatize the acid functions activated in the hydrogel. The nitrocellulose slides were blocked in the same manner as the membranes.

2. Labeling of the Glycoproteins
Biotinylation:

0.1 mL of a 10 mg/mL solution of biotin-NHS ester in DMF were added to a solution of the glycoprotein (2-4 mg) in 0.4 mL of $NaHCO_3/Na_2CO_3$ buffer (50 mM, pH 9.0). The mixture was stirred at 25° C. for 2 h and the biotinylated glycoproteins were then purified by size exclusion chromatography using PBS as the mobile phase. The labeled proteins were stored at 0° C. as 1-2 mg/mL solutions in PBS.

Fluorescent Label:

The glycoproteins (2-4 mg) were conjugated with the Hilyte Plus™ 647 labeling kit from AnaSpec, Freemont, USA (a cy5 analog) and purified by following the protocol described by the manufacturer. The labeled proteins were stored at 0° C. as 1-2 mg/mL solutions in PBS. The fluorescently labeled proteins can be analyzed directly in the gel with a gel viewer before or after the transfer.

3. Sodium Dodecyl Sulfate-Polyacrylamide Gel Electrophoresis (SDS-PAGE).

The labeled proteins (with biotin or fluorophore) (1 mg/ml) (1:10, 1:20 and 1:100) were treated with reducing loading buffer (5 minutes at 90° C.) and 10 µl of these dilutions were added to the SDS-PAGE gel (12% acrylamide, 1.0 mm). The electrophoresis was performed in TGS buffer (tris-glycine buffer containing 10% SDS) at 100 V for 1 hour. The transfer was performed at 100 V for 1 hour.

4. Transfer of the Glycoproteins to a Surface Containing the Microarray of Lectins.
Electrophoretic Transfer:

The transfer on the nitrocellulose or PVDF membranes was performed in TG buffer containing 20% MeOH at 100V for 1 h. After the transfer, the membranes were washed for 1 hour at room temperature Non-Electrophoretic Transfer:

Before the transfer, the gel containing the glycoproteins separated by their molecular weight was treated with fixing buffer (MeOH/$H_2O$, 5% AcOH) for 30 min. The gel was then rinsed with $H_2O$ and left to air-dry for 10 min to improve the adherence of the gel on the surface on which the glycoproteins are to be transferred. The gel is placed on filter paper and the slide containing the microarray of lectins is placed on the gel. This gel/slide sandwich is placed between two glass plates and a weight of 1 Kg is applied on this surface. This system is placed in a wetted plastic container and heated at 37° C. for 2 h. After this time, the slides are removed from the gel and washed with $H_2O$. The surface containing the glycoproteins interacting with the lectins is ready to be analyzed. By means of this diffusion transfer only a small amount of the glycoprotein is transferred, therefore the gel can be reused for a number of transfers or be analyzed after the transfer to confirm the presence and the position of the glycoproteins in the gel.

5. Detection of the Glycoproteins Labeled with Biotin:

The membranes or slides containing the microarrays of lectins were incubated after the transfer of the biotinylated glycoproteins with a neutravidin-cy5 conjugate with a concentration of 2 µg/mL in PBS containing 0.5% Tween-20 for 1 h at 25° C. The neutravidin (Invitrogen, Oregon, USA) was conjugated with the Hilyte Plus™ 647 labeling kit from AnaSpec, Freemont, USA (a cy5 analog) following the protocol described.

The nitrocellulose membranes or slides containing the glycoproteins labeled with a fluorophore or interacting with fluorescent neutravidin were analyzed in a gel viewer (VersaDoc, BioRad) or in a Leica DMI 6000B epifluorescence microscope (Leica, Wetzlar, Germany).

The slides coated with a functionalized hydrogel were analyzed in a fluorescence scanner for microarrays (Agilent Technologies, Santa Clara, USA).

Since the microarrays of lectins contain a fluorophore alternative to cy5 (0.01% BSA-cy3), the situation of the microarrays printed in the slide can be analyzed in a second channel with the fluorescence scanner.

6. Interpretation of the Results:

The images obtained by the gel viewer were processed with the applications included in the software of the equipment.

The images obtained in the epifluorescence microscope could be analyzed as grayscale images with the Adobe Photoshop CS4 software.

The images obtained by the fluorescence scanner for microarrays were analyzed with the ProScanArray®Express software (Perkin Elmer). The fluorescence intensities are shown in the form of an excel spreadsheet which includes the number, name and position in the slide of the lectins, as well as the point and mean fluorescence values, the background measurement and the standard deviation of each spot. These data simplify to a great extent the interpretation of the images and the comparative analysis between different glycoprotein samples.

Example 1

The protein mixtures are biotinylated with a biotinylation kit according to standard procedures. After the biotinylation, the proteins are separated into one or two dimensions by means of SDS-PAGE according to their mass as usual. The proteins are then transferred to an especially prepared membrane which has been previously stamped with multiple copies of small arrays of lectin using a standard wet or semi-dry electrophoresis apparatus. The arrays of lectin cover the entire membrane in the form of a large array, not unlike a TV screen with 4 different colored pixels for each individual point. See FIG. 1.

During the transfer process, all the proteins in the gel are transferred to the membrane, maintaining their relative x,y positions as in a normal immunotransfer. However, the transfer membrane has been treated with a blocking agent after stamping the lectins to prevent the non-specific binding of proteins to the membrane. The glycosylated proteins are only bound according to their binding affinities for the individual lectins present in the array. During the transfer process, each glycoprotein moves through the gel towards the membrane and interacts with the individual lectins present in the arrays. For the principle to work, the protein bands in the gel cover at least one entire array of lectins such that all the lectins included in the array are subjected to interaction with the protein which moves from the gel to the membrane.

The glycoproteins bind to the array of lectin through their terminal sugars or sugar epitopes recognized by the individual lectins. The other non-glycosylated proteins cannot bind to the support and are removed in the washing step. In order to have a background signal it is very important to block the membrane after stamping the lectins. To visualize the proteins bound to the arrays of lectins and their glycosylation pattern, the membrane is incubated with fluorescently labeled streptavidin, washed again and examined with a fluorescence microscope or a gel viewer (for example, versa-doc, Biorad). The individual arrays are immediately identified by one or more control spots (where biotinylated lectins have been stamped). The intensities for the individual spots depend on the amount and the strength of the sugar-lectin interactions. The type of sugar is defined by the position of the lectin interacting in the array.

Multiple glycoproteins can be analyzed simultaneously in individual arrays of lectin in the membrane and their glycan composition can be evaluated.

The change of glycosylation, which is frequently a specific characteristic of a disease, type of tissue, species, age or development state, can be easily identified and followed in complex protein mixtures.

In a first prototype, 7 lectins have been included in a single array, next to two labeled lectins which establish the orientation of the array and the buffer as control. All the spots are printed in duplicate. The studies indicate that due to the large size of the bands for proteins in SDS-PAGE gels compared to the size of the arrays of lectins, additional lectins can easily be integrated together with the array, which allows an even more refined analysis of the glycosylation of proteins.

Figure 2:
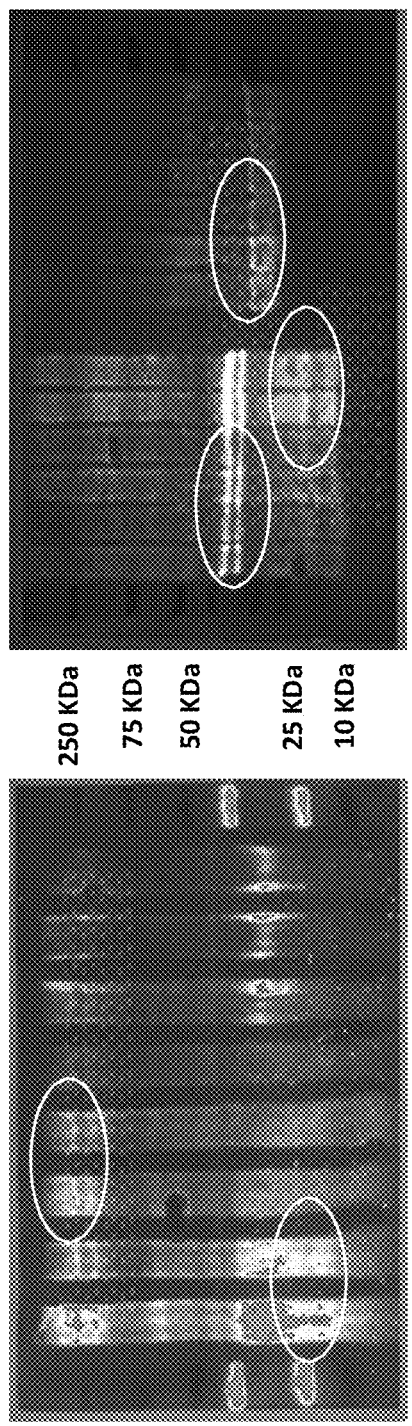
FIG. 2. Image of the gel viewer of the nitrocellulose membrane after the transfer and the incubation with neutravidin-cy5. The biotinylated proteins are separated by their molecular weights: porcine thyroglobulin (300 KDa, left figure), ovalbumin (44 KDa, right figure), soy bean agg. (24 KDa, right figure) and WGA (14 KDa, right and left).

Firstly, several biotinylated proteins (porcine thyroglobulin (300 KDa, left figure), ovalbumin (44 KDa, right figure), Soy bean agg. (24 KDa, right figure) and WGA (14 KDa, right and left)) were fractionated in parallel by means of polyacrylamide gel electrophoresis under denaturing conditions. After the fractionation, the proteins were transferred to a nitrocellulose membrane which had been uniformly coated with arrays which contained WGA, ConA, RCA, PSA, SNA, BS-1B and UEA-1 and 4 points of biotinylated ovalbumin as control. The membrane was then incubated with neutravidin-cy5. The appearance of the membrane after the visualization of the fluorescence emitted by Cy5 is shown in FIG. 2.

Figure 3A:
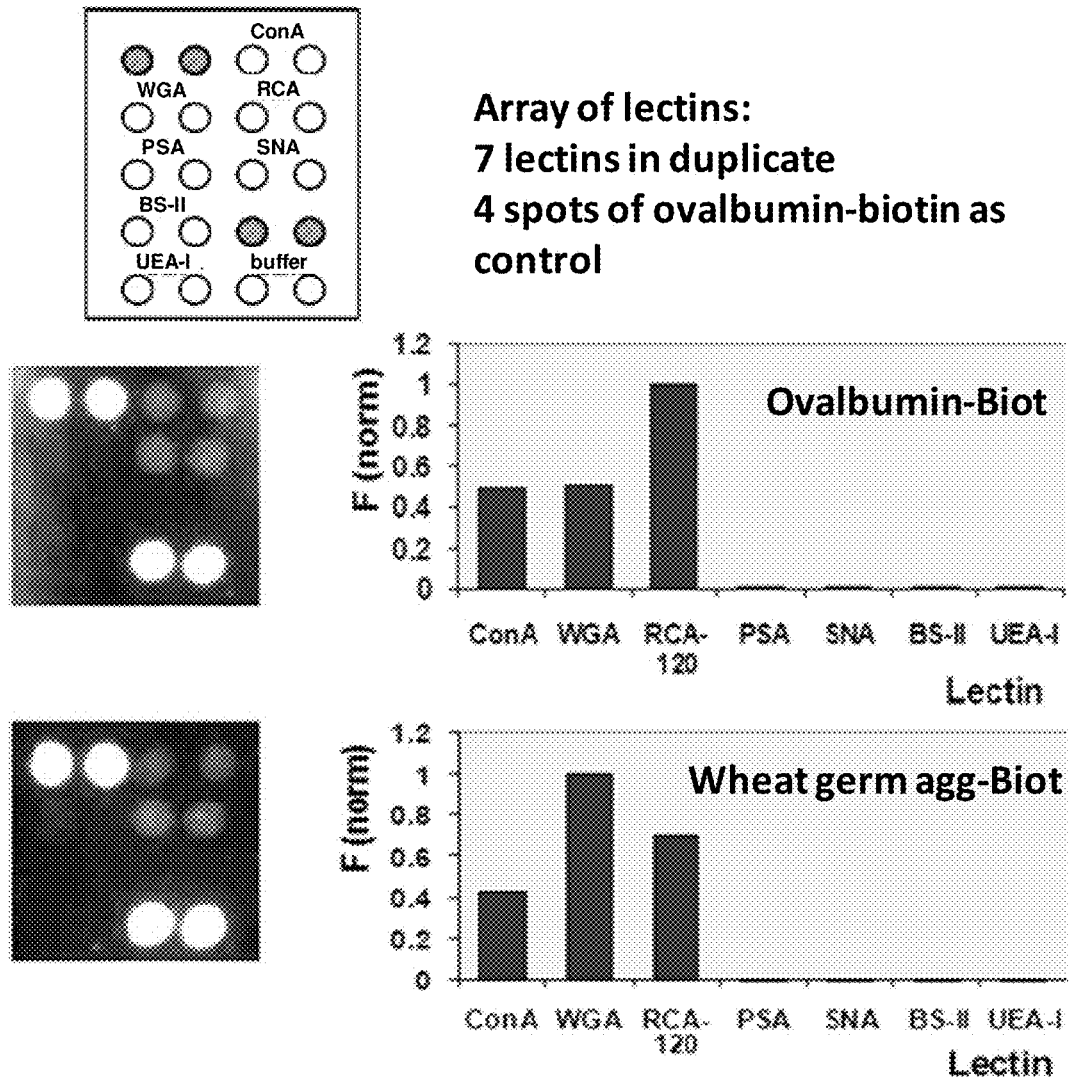
FIG. 3. Epifluorescence microscope images of the arrays of lectins of the cellulose membranes after the transfer and detection with neutravidin-cy5. The histograms correspond to the standardized fluorescence obtained from the VersaDoc gel viewer from BioRad.
Figure 3B:
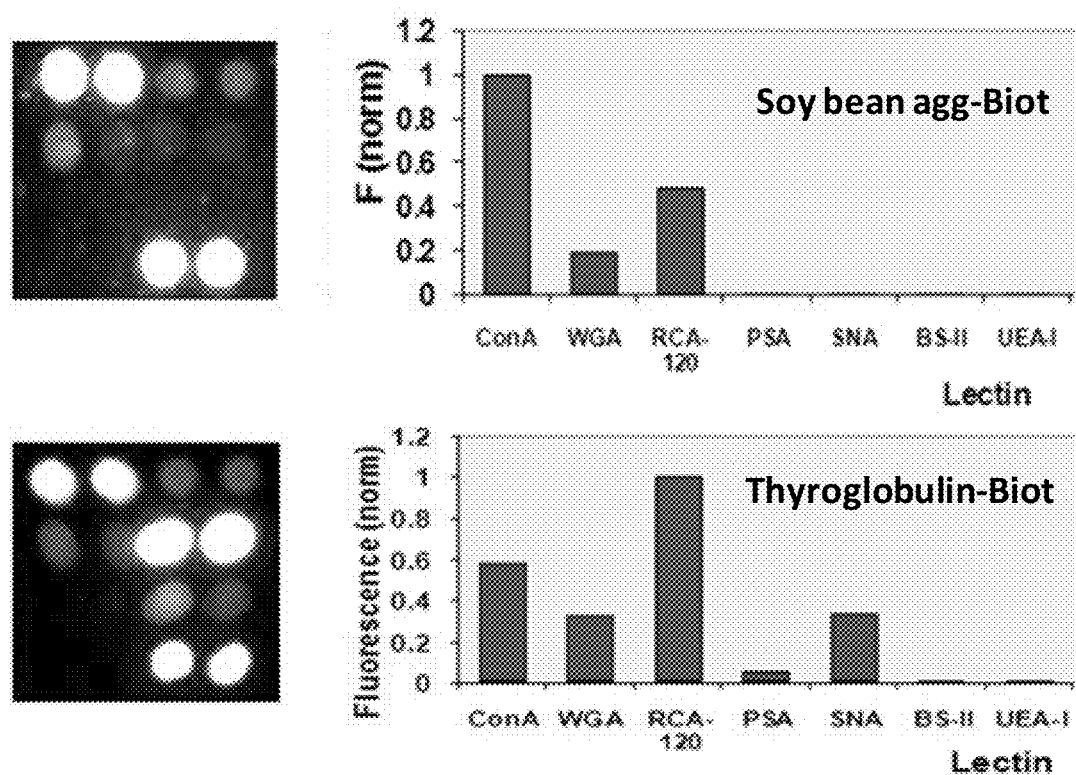

The membrane generated according to the aforementioned method was then analyzed by means of epifluorescence microscopy (FIG. 3). The intensity of the standardized fluorescent signal in each of the cells of the array was determined using the software of the VersaDoc gel viewer from BioRad and depicted in the histograms shown in FIG. 3. It is observed that every for at least 4 of the transferred glycoproteins, a characteristic cell pattern of the array with fluorescent signal was observed, indicative of the specific interaction of each of the glycoproteins with the different lectins of the array.

Figure 4:
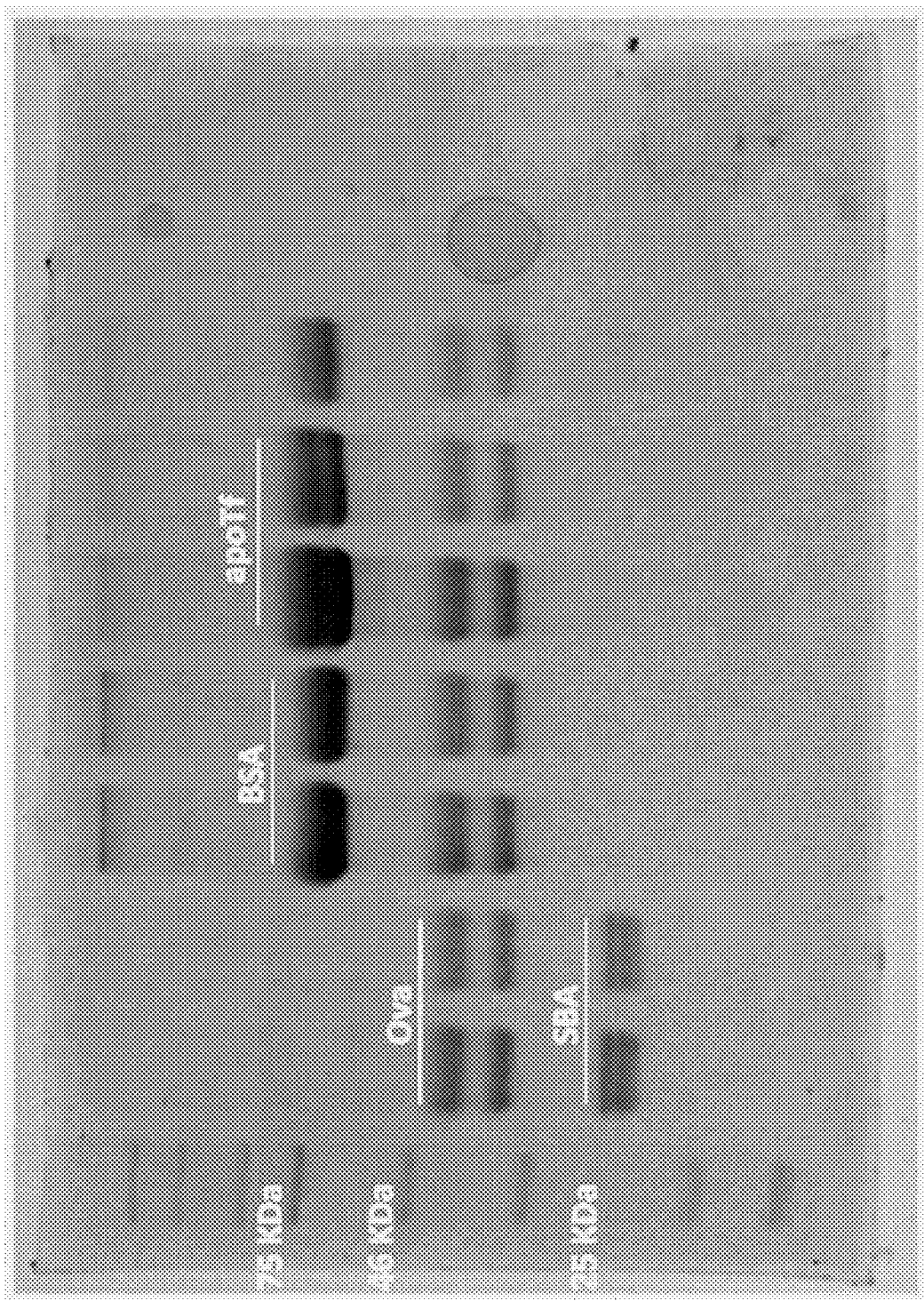
FIG. 4. Staining of the gel with Coomassie blue after a non-electrophoretic transfer on a glass slide containing the array of 16 lectins.
Figure 5:
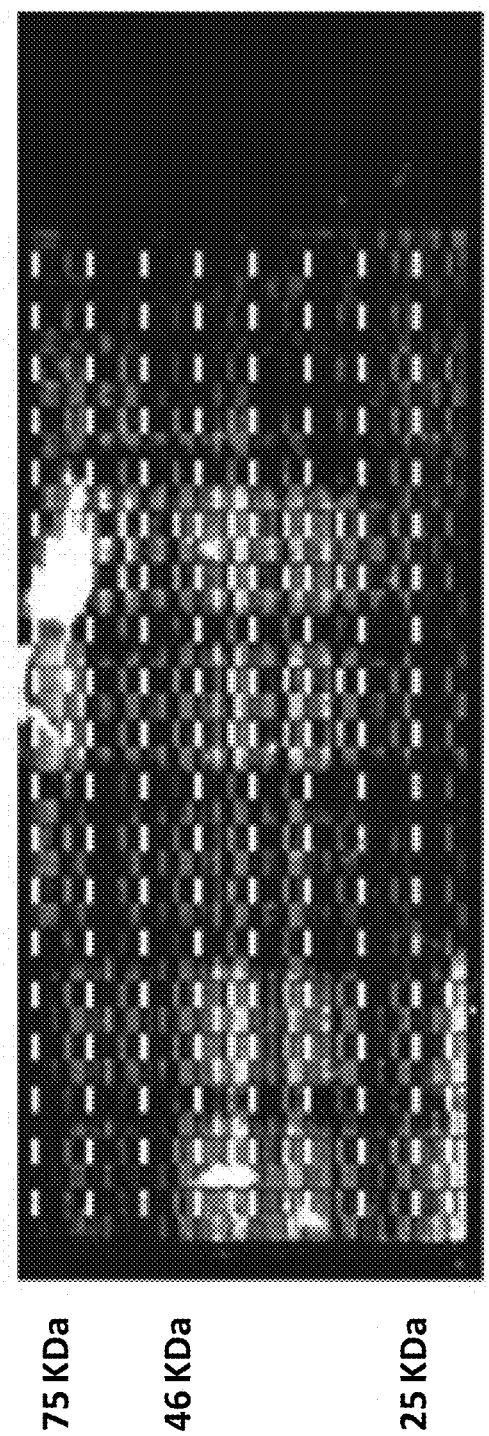
FIG. 5. Image of the whole slide after the non-electrophoretic transfer and detection with neutravidin-cy5. The image was obtained with an Agilent G265BA microarray scanner.

Different biotinylated glycoproteins (Ovalbumin, SBA, BSA and apotransferrin) were then fractionated by means of polyacrylamide-SDS gel electrophoresis. The proteins were transferred in a non-electrophoretic manner from the gel to a glass support containing the array of 16 lectins. FIG. 4 shows the gel stained with Coomassie blue after a non-electrophoretic transfer. FIG. 5 shows the image of the entire slide after the non-electrophoretic transfer and detection with neutravidin-cy5. The image was obtained with an Agilent G265BA microarray scanner.

Figure 6:
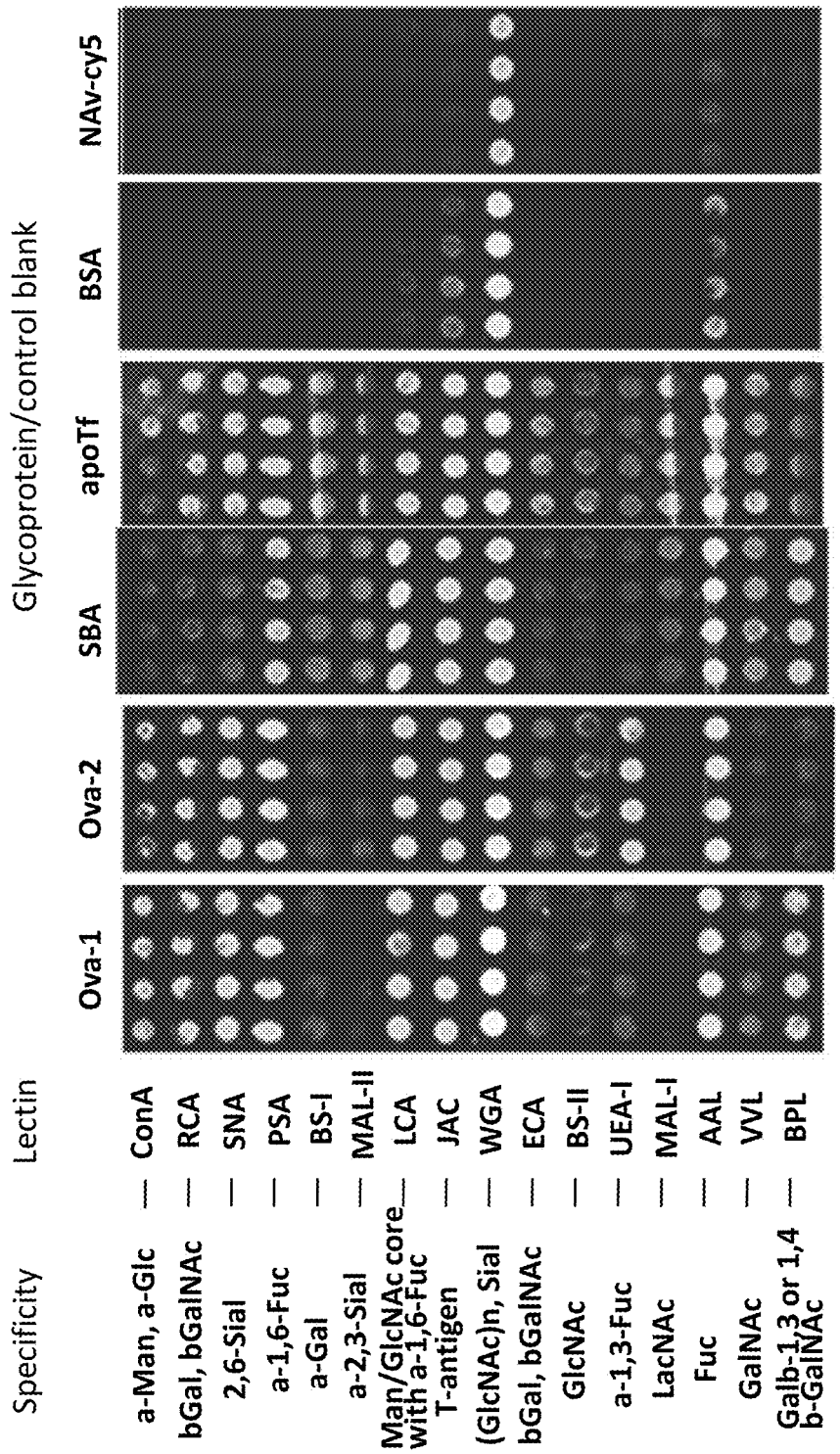
FIG. 6. Glycosylation profiles of different glycoproteins transferred to a slide containing the array of 16 lectins.
Figure 7A:
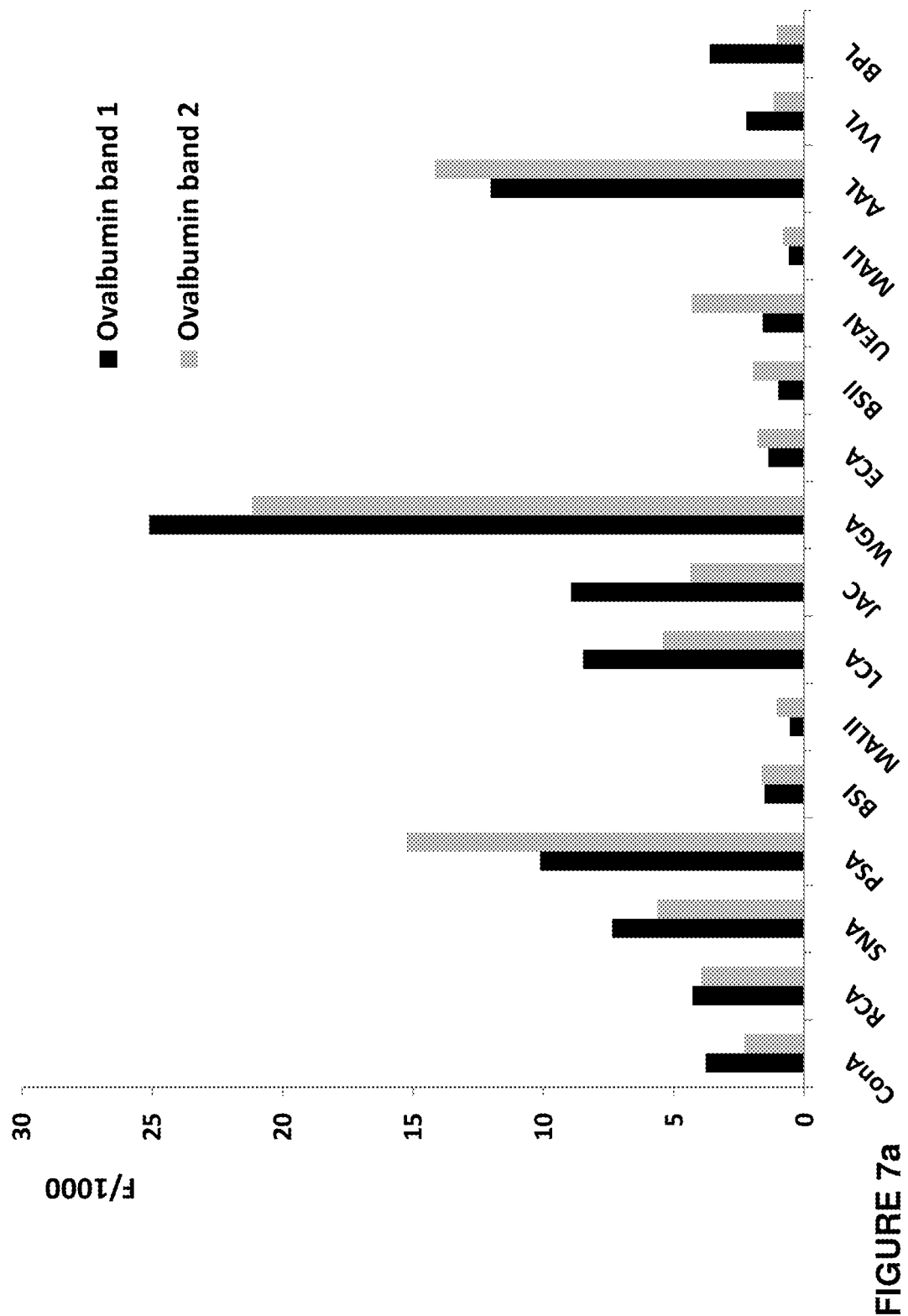
FIG. 7. Histograms showing the glycosylation profile of the different glycoproteins or glycoforms of the same protein in the form of relative intensities corresponding to the interaction with the array of lectins. The data were obtained by means of processing the images with the ProScanArray®Express software (Perkin Elmer).
Figure 7B:
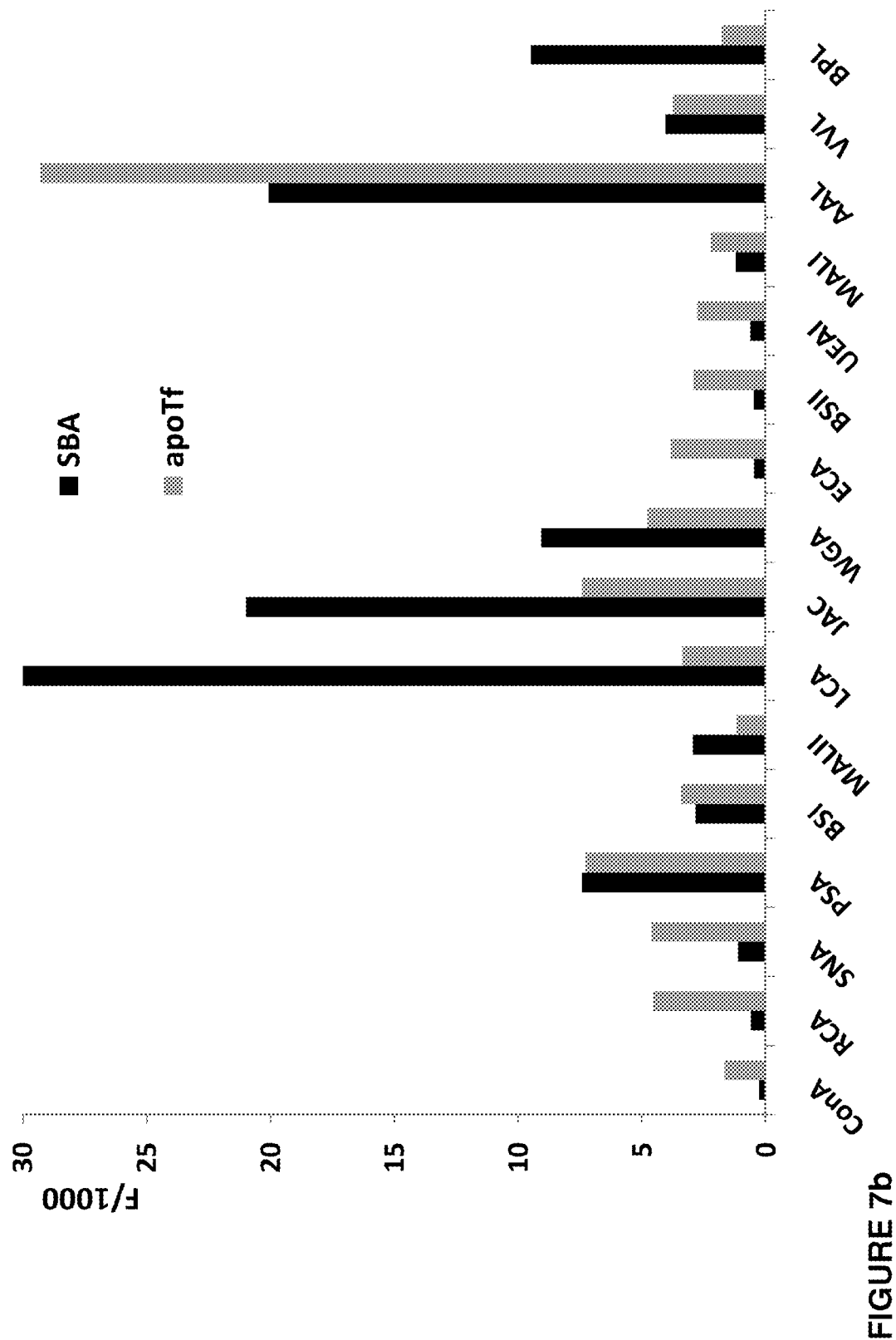

FIG. 6 shows the glycosylation profiles of different glycoproteins transferred to a slide containing the array of 16 lectins. The glycosylation profile of the different glycoproteins or glycoforms of the same protein in the form of relative intensities corresponding to the interaction with the array of lectins is shown. The quantification of the data obtained in said experiment for three of the proteins analyzed in said experiment (ovalbumin, appearing in two bands, SBA and apotransferrin) is shown in FIG. 7 as histograms.

Figure 8:
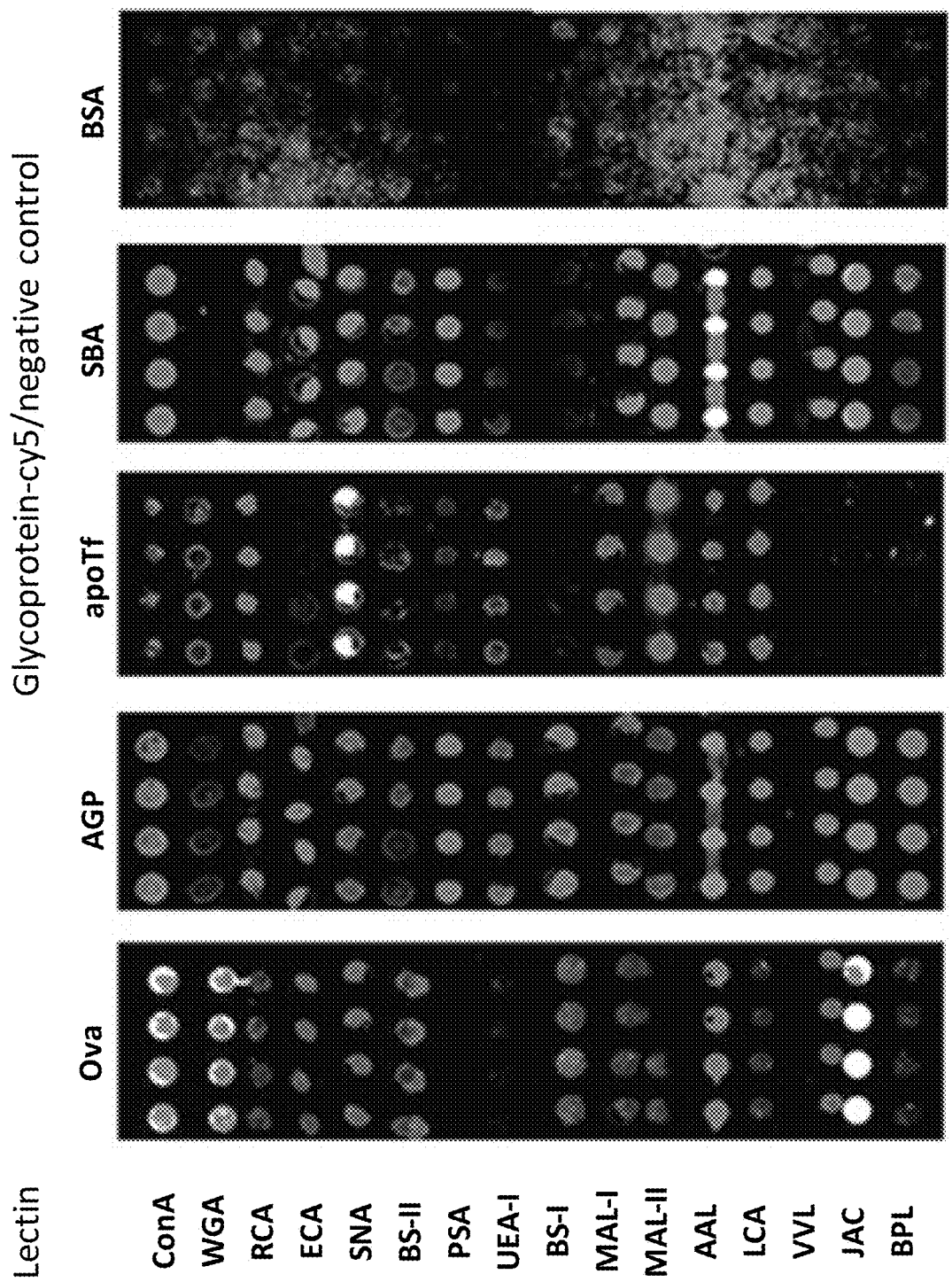
FIG. 8. Glycosylation profiles of different fluorescently labeled glycoproteins transferred to a slide containing the array of 16 lectins.
Figure 9:
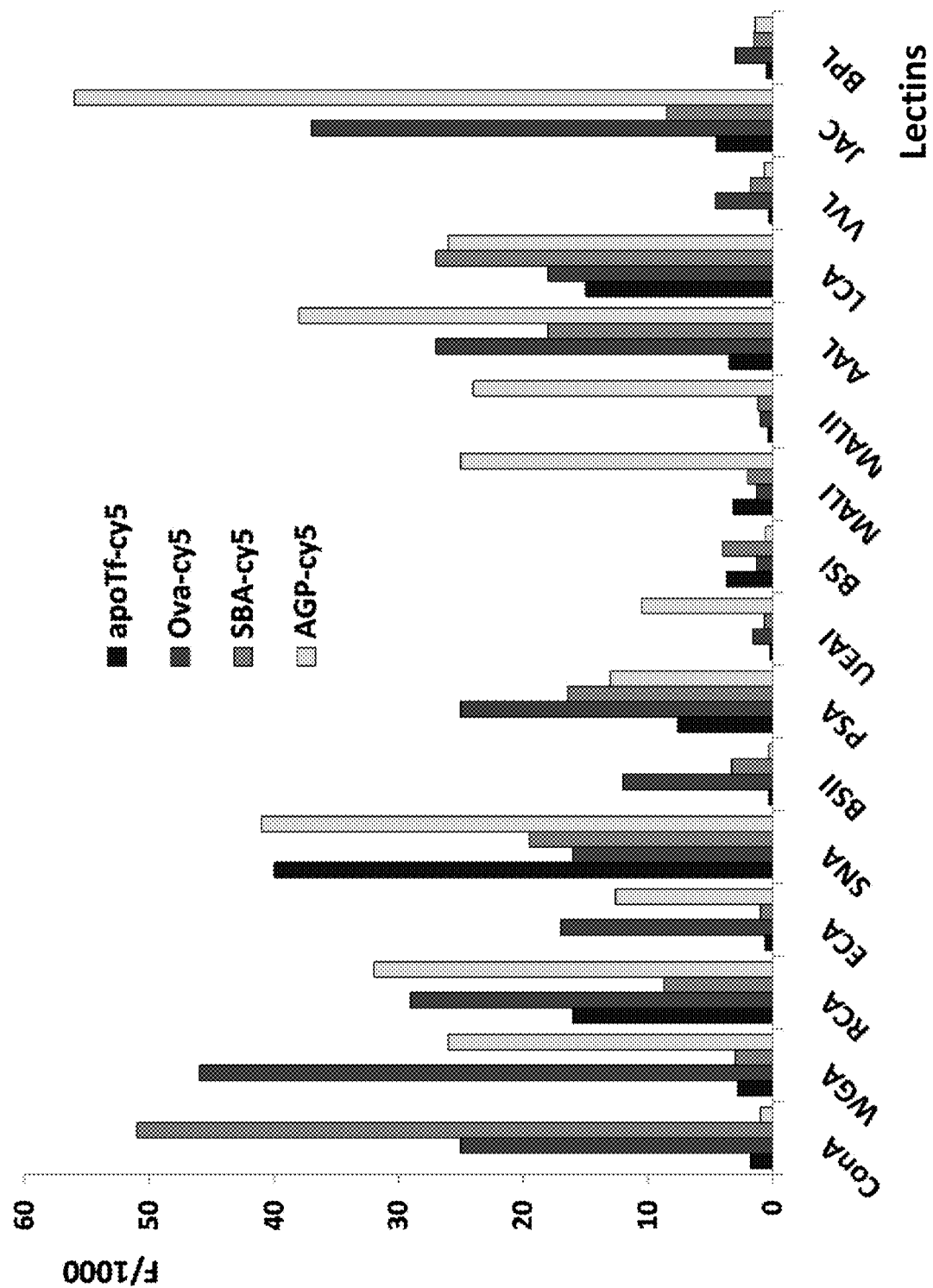
FIG. 9. Histograms showing the glycosylation profile of the different fluorescently labeled glycoproteins in the form of relative intensities corresponding to the interaction with the array of lectins. The data were obtained by means of processing the images with the ProScanArray®Express software (Perkin Elmer).

Secondly, several proteins (ovalbumin, AGP, apotransferrin, SBA and BSA) previously labeled with Cy5 were fractionated in parallel. After the fractionation, the proteins were transferred to a glass support which had been uniformly coated with arrays of lectins which contained 16 lectins. FIG. 8 shows the glycosylation profiles of different glycoproteins transferred to the slide. The histograms corresponding to the quantification of the relative intensities for the 4 proteins are shown in FIG. 9.

Example 2

Materials and Methods
1. Microarray Fabrication

Lectins, Concanavalin A (ConA), Wheat germ agglutinin (WGA), *Ricinus communis* agglutinin (RCA), *Erythrina cristagalli* (ECA), *Sambucus nigra* lectin (SNA), *Maackia amurensis* lectin I (MAL-I), *Aleuria aurantia* lectin (AAL), *Ulex europaeous* agglutinin I (UEA-I), *Pisum sativum* agglutinin (PSA), *Lens culinaris* agglutinin (LCA), *Galantus nivalis* (GNA), *Narcissus pseudonarcissus* lectin (NPL), *Griffonia* (Bandeiraea) *simplicifolia* lectin II (BSL-II), *Phaseolus vulgaris* E+L (PHA), Jacalin (JAC), *Wisteria floribunda* lectin (WFL), *Vicia villosa* lectin (VVL), Peanut agglutinin (PNA), *Lotus tetragonologus* lectin (LTL) and *Griffonia* (Bandeiraea) *simplicifolia* lectin I (BSL-I) were purchased from Vector laboratories, Burlingame, USA and Sigma-Aldrich. Lectins were reconstituted in HEPES 50 mM, pH 8.5, 0.3 mM $Ca^{2+}$, 0.08% $NaN_3$ as 2.0-5.0 mg/mL solutions and stored at −20° C.

Lectin solutions, 0.4-0.5 mg/mL were prepared in print buffer (1.0 mM D-glucose in PBS containing 0.01% of cy3-conjugated BSA). Aliquotes, 20 uL, of each freshly prepared solution were loaded in a 384 well plate which can be stored overnight at 4° C. IgG free BSA was purchased from Sigma-ALdrich and was labeled with Hilyte Plus™ 555 (cy3 analogue) protein labeling kit form AnaSpec, Freemont, USA following the protocol described there.

Volumes (0.33 nL) of these dilutions were spotted onto NHS functionalized glass slide (Nexterion®H, Schott AG, Mainz, Germany) with a 0.2 mm spacing between spot centers with a non-contact piezoelectric spotter (Piezoarray from Perkin Elmer, Shelton, USA):

Lectin array v1.0 consisted in 99×360 (columns/rows) spots covering the whole slide surface (36000 spots/slide) with a single lectin, WGA or ConA.

Lectin array v2.0 consisted in 11×1 (spot columns/rows) subarrays and in multiple matrixes 9×225 (array columns/rows) covering the whole slide surface (22275 spots/slide) with 10 lectins, ConA, WGA, RCA, ECA, SNA, MAL-I, AAL, UEA-I, LCA and JAC. Printing buffer was also printed as a negative control.

Lectin array v3.0 consisted in 21×1 (spot columns/rows) subarrays and in multiple matrixes 4×280 (array columns/rows) covering the whole slide surface (23520 spots/slide) with all the set of lectins including printing buffer as a negative control. For the analysis of urinary glycosylation the negative control was substituted for uromodulin antibody printed at 0.1 mg/mL.

The humidity in the print chamber was maintained around 50% before and during printing. The slides containing the lectin arrays were incubated after printing in a 75% humidity chamber at 18° C. overnight and stored at −20° C. without quenching if not used immediately.

The remaining NHS groups were quenched by placing the slides in a 30 mM ethanolamine solution in borate buffer for 1 h and blocked with a 0.3 mg/mL BSA, 0.3 mM Ca2+ solution in PBST0.05 for 1 hour. The slides were directly dried by centrifugation without any washing step.

2. Sample (Protein Mixture) Preparation

The proteins analyzed in this study: fetuin from calf serum, albumin from chicken egg white, bovine ribonuclease B and IgG free BSA were purchased from Sigma-Aldrich.

Glycoprotein samples were prepared as 2.0 mg/ml total protein solutions in PBS, this solution was diluted 1:2 with phosphate buffer, pH 8.5 for labeling and treated with 1 ul of dye (Hilyte Plus™ 647(cy5 analogue) protein labeling kit form AnaSpec, Freemont, USA) for each 100 uL of sample, for 2 hours at room temperature. Dye excess was removed using the columns included in the kit or by buffer exchange to PBS employing 3 kDa amicon filters. The labeled glycoproteins were stored as 1-2 mg/mL solutions in PBS. Crude samples can be also directly loaded in the gel, the dye excess runs first under SDS-PAGE and does not contaminate the gel.

Protein mixture from human urine was obtained by buffer exchanging and concentration of urine samples with Vivaspin filters. The mixture in PBS was labeled and stored as solutions with 1.0 optical density (O.D.).

Labeled glycoproteins (0.1 to 1 µg/10 µll) were treated with 10 µl of reductive sample buffer (5 min at 90° C.) and these solutions were added to the SDS-PAGE gel (12% polyacrylamide, 1.0 mm). Electrophoresis was performed in TGS buffer at 150 V for 1.0 h at 4° C.

3. Non-Electrophoretic Blotting

Previous to the blotting the gel was treated with fixing buffer (MeOH/$H_2O$, 5% AcOH) for 30 minutes. Then the gel was slightly washed with PBS (1 minute) and with blocking solution 0.4 mg/mL BSA, 0.3 mM $Ca^{2+}$ solution in PBST0.05 for 3 min and left to air dry for 30 minutes in order to adhere to the membrane or glass slide containing the lectin array. The gel/slide sandwich was placed on a filter paper. The sandwich was placed between two glass plates and 1 Kg weight was placed on top. This sandwich was placed in a pre-warmed humidified plastic container and incubated at 37° C. for 60 minutes. The slides were removed from the sandwich and washed with PBS for 5 min. The surface containing the transferred glycoproteins interacting with the lectin array is ready for analysis. Only a small amount of the glycoprotein is transferred so the gel can be reused for a number of blottings or also stained post-lectin blotting to confirm the presence and position of the proteins in the gel.

4. Lectin Panel:

(Print buffer: 1 mM D-Glucose in PBS Containing 0.01% of cy3-Conjugated BSA)

| | Lectin | Abbrev | Print concentration | Selectivity | Sugar |
|---|---|---|---|---|---|
| 1 | *Conavalia ensiformis* | ConA | 0.5 mg/mL | Branched/terminal Man, terminal GlcNAc, α-Glc | Mannose |
| 2 | *Triticum vulgaris* | WGA | 0.5 mg/mL | (GlcNAc)n, sialic | GlcNAc |
| 3 | *Ricinus communis* | RCA | 0.5 mg/mL | β-Gal, Lac, LacNAc | Galactose |
| 4 | *Erythrina cristagalli* | ECA | 0.5 mg/mL | Gal, GalNac | Galactose |
| 5 | *Sambucus nigra* | SNA | 0.5 mg/mL | α-2-6 sialic acid on LacNAc | Sialic acid |
| 6 | *Maackia amurensis* | MAL | 0.5 mg/mL | α-2-3 sialic on Gal/GalNAc | Sialic acid |
| 7 | *Aleuria aurantia* | AAL | 0.4 mg/mL | Fuc | Fucose |
| 8 | *Ulex europea-I* | UEA-I | 0.5 mg/mL | α-1,2-Fuc | Fucose |
| 9 | *Pisum sativum* | PSA | 0.5 mg/mL | Fuc α-1,6GlcNAc and α-Man | Fucose |
| 10 | *Lens culinaris* | LCA | 0.5 mg/mL | Complex (Man/GlcNAc core with α-1,6 Fuc) | Fucose |

| Lectin | Abbrev | Print concentration | Selectivity | Sugar |
|---|---|---|---|---|
| 11 Galanthus nivalis | GNA | 0.4 mg/mL | Terminal α-1,3Man | Mannose |
| 12 Narcissus pseudonarcissus | NPL | 0.4 mg/mL | Terminal and internal Man | Mannose |
| 13 Bandeirae simplicifolia-II | BSII | 0.5 mg/mL | Terminal GlcNAc | GlcNAc |
| 14 Phaseolus vulgaris | PHA | 0.5 mg/mL | Tri/tetraantennary oligos | Galactose |
| 15 Jacalin | JAC | 0.4 mg/mL | T antigen | GalNAc |
| 16 Wisteria floribunda | WFA | 0.5 mg/mL | GalNAc | GalNAc |
| 17 Peanut agglutinin | PNA | 0.5 mg/mL | T antigen, Gal(|β-1,3)GalNAc | Galactose |
| 18 Vivia villosa B4 | VVL | 0.5 mg/mL | GalNAc | GalNAc |
| 19 Lotus tetragonolobus | LTL | 0.5 mg/mL | Terminal α-Fuc, Lewis$^x$ | Fucose |
| 20 Bandeirae simplicifolia-I | BS-I | 0.5 mg/mL | α-Gal | Galactose |
| 21 Anti Tamm-Horsfall glycoprotein | Anti-THP | 0.1 mg/mL | THP | |
| 21 Print buffer | | | | |

Results

Figure 10A:
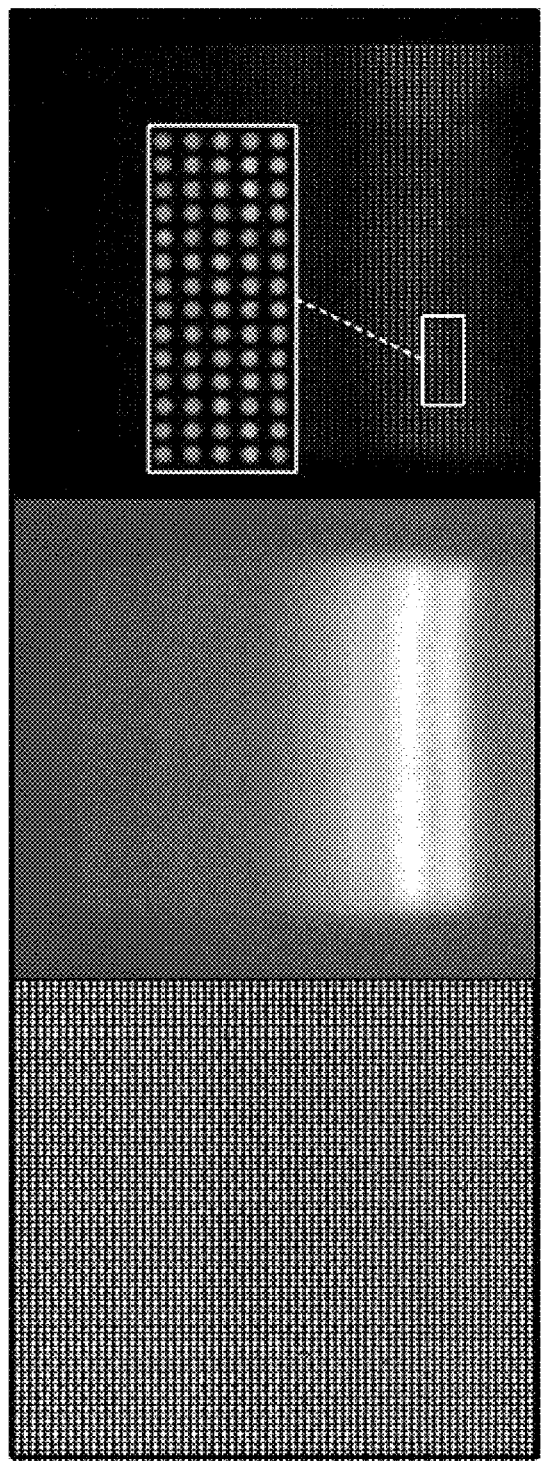
FIG. 10. a) Protein transfer by diffusion to a lectin functionalized glass slide covered with over 36000 printed spots of covalently attached wheat germ agglutinin (WGA). b) Transfer of a BSA/RNAseB mixture to a slide printed with Concanavalin A (ConA). c) Optimization of the diffusion transfer in terms of applied pressure and incubation time.

As a proof of principle, protein transfer was tested by diffusion to a lectin functionalized glass slide covered with over 36000 printed spots of either covalently attached wheat germ agglutinin (WGA) or Concanavaline A (Con A) at 200 μm spacing, which equals a digital display resolution of 130 dpi (dots per inch) (FIG. 10a left). WGA binds chitobiose including the Man (β-1,4)GlcNAc (β-1,4)GlcNAc trisaccharide conserved in all N-glycans and has been used as an universal lectin for detecting the presence of N-glycans in general. Con A is a mannose binding lectin with particular affinity towards high mannose glycans. As test proteins RNAse B, a 15 kDa glycoprotein with a single N-glycosylation site, occupied by 5 different high mannose structures, and unglycosylated bovine serum albumin (BSA) as a negative control was chosen to assess binding due to non-specific interaction. Both proteins were tagged with cyanine-5 prior to SDS-PAGE electrophoresis. After gel-electrophoresis on a 1 mm slab polyacrylamide gel under reducing conditions, the proteins were fixed with acetic acid in methanol to minimize lateral diffusion, washed with PBST buffer, air-dried for 10 minutes and covered with a WGA-functionalized slide. This sandwich was then placed between filter paper and glass plates and incubated in a sealed container at a humidity of 80% and applying a pressure of x g/cm$^2$ for 1 hour. The slide was separated from the gel, washed, dried by centrifugation and analyzed in a fluorescence scanner, while fluorescent RNAse gel bands were visualized in a gel-visor (FIG. 10a).

Figure 10B:
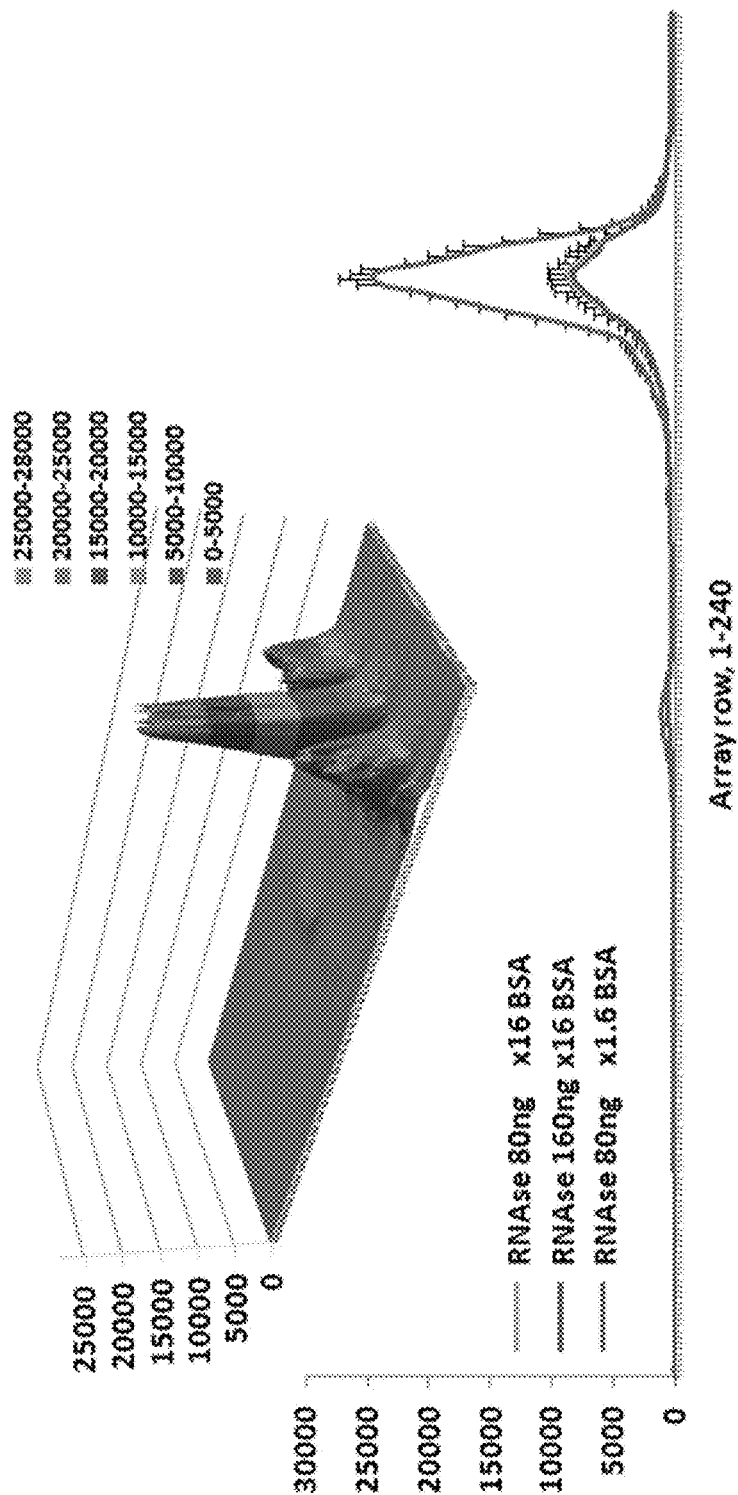
Figure 10C:
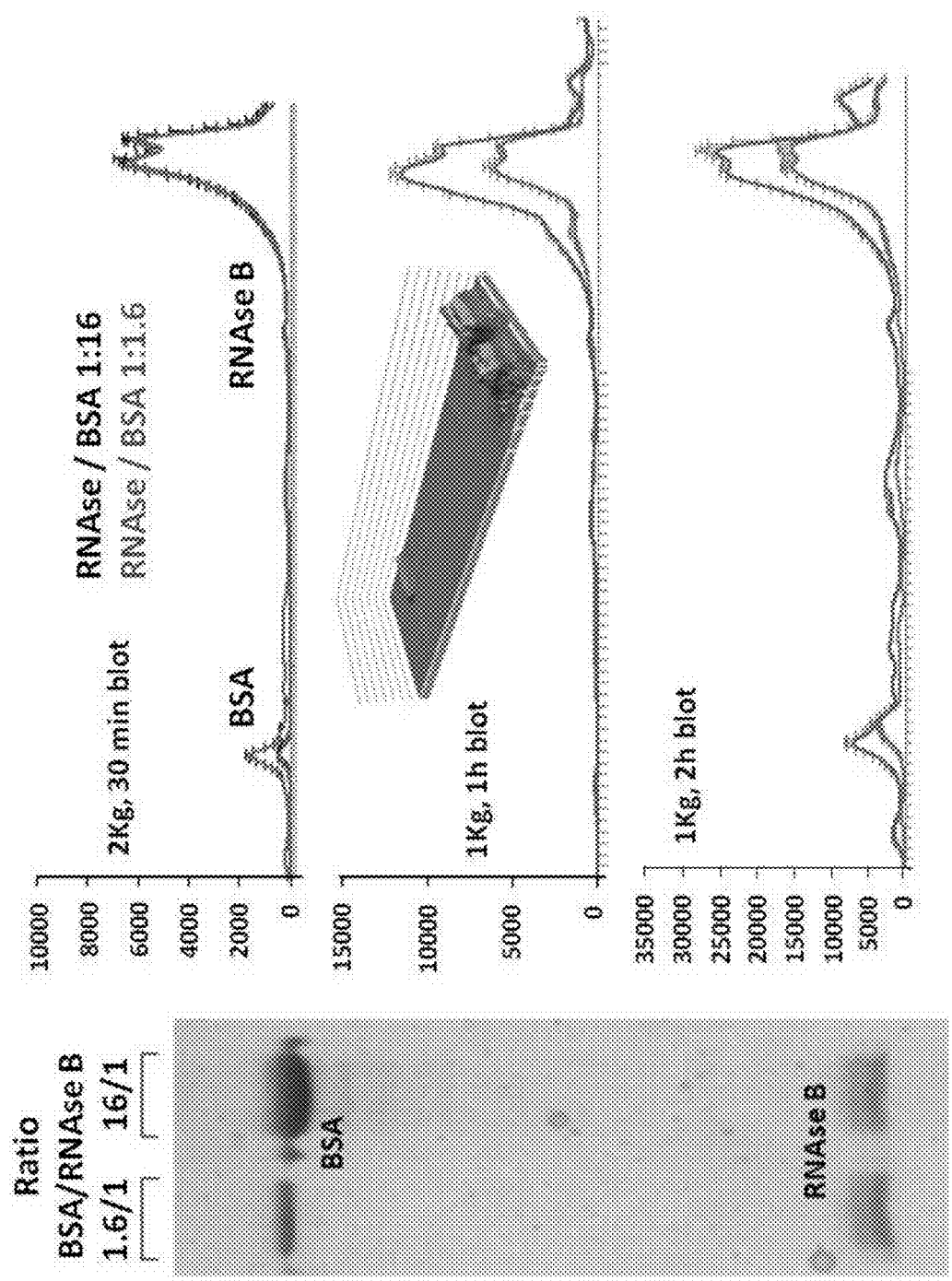

The scanned fluorescence images showed only bands for the trapped glycoprotein and no BSA binding for both affinity surfaces at low excess ratios of BSA (FIGS. 10b and 10c). Even with 10-fold increase of the BSA concentration with respect to RNAse, only very low binding was observed for the WGA surface while BSA did not bind at all to the ConA spotted surface (FIGS. 10b and 10c).

In the method herein disclosed, incubation for 30 minutes usually showed sufficient protein transfer, while incubation times >2 hours resulted in saturation especially for low weight proteins. Incubation was carried out at 37° C. to ensure reasonable transfer rates without risking lectin denaturation and a humidity chamber was employed to avoid extensive drying of the gel during transfer resulting in non-specific binding and deformation of the gel. In an attempt to shorten incubation times the pressure employed was increased during protein diffusion transfer. The results shown in FIG. 10c demonstrate that doubling the incubation pressure can shorten the incubation time by 50% but increases slightly non-specific interaction of BSA with WGA surface and results in less well resolved glycoforms, while the amount of transferred RNAse B is similar to 1 h incubation at half the pressure. No lectin-carbohydrate interaction was observed. However when increasing the pressure four-fold and lowering incubation time to 15 minutes, in line with reported minimum equilibrium times for lectin/carbohydrate interactions.

Figure 11:
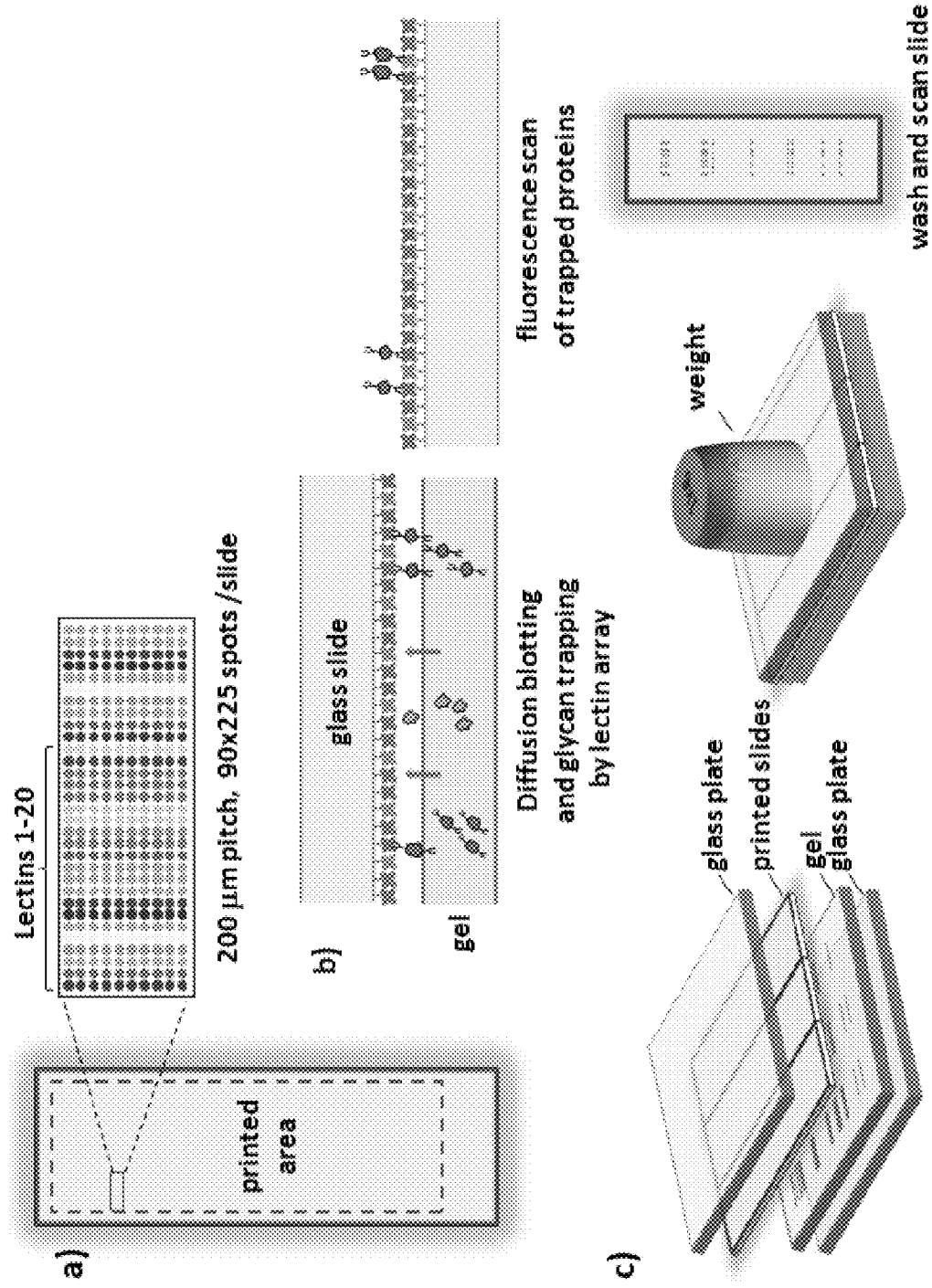
FIG. 11. Schematic depiction of the glycoprotein blot by diffusion to glass slides printed with the lectin array.

In a first attempt, the glycoprotein trapping by an 10 lectin array comprising concanavalin A, (ConA), wheat germ agglutinin (WGA), Ricinus communis agglutinin (RCA), Erythrina cristagalli lectin (ECA), Sambucus nigra agglutinin (SNA), Maackia amurensis lectin (MAL-1), Aleuria aurantia lectin (AAL), Ulex europeus agglutinin (UEA), jacalin lectin (JAC), Lens culinaris agglutinin (LCA) and printing buffer as a control was investigated. The lectins were printed in rows forming multiple 1×11 arrays with the high resolution in the direction of electrophoretic separation, FIG. 11 (array design). FIG. 11a shows that fluorescently tagged proteins can be separated by gel electrophoresis and then diffusion-blotted onto a glass slide covered with multiple copies of micrometer size lectin arrays. Here the glycoproteins are sorted and trapped by specific lectin-carbohydrate interactions on the slide (FIG. 11b). After transfer and washing off unbound material the slide is scanned and the images analysed with dedicated software (FIG. 11c). The fluorescence intensity of individual spots is a direct measure for the affinity between a present carbohydrate epitope and the spotted lectin. Knowledge of the lectin binding specificities then allows to generate a picture of the glycan epitopes present on the individual glycoproteins.

After optimisation to avoid non-specific interaction and to compensate for extreme affinity differences lectin printing concentrations were set to 0.5 mg/ml except for GNP, LCA and JAC which were printed at 0.4 mg/ml. Essential in avoiding non-specific interaction was also the use of an optimized incubation buffer containing BSA and calcium.

Commercial bovine serum fetuin, a 48.2 kDa glycoprotein with 3 N- and 3 O-glycosylation sites was chosen to investigate the potential of lectin array blotting for the analysis of protein glycosylation.

Figure 12A:
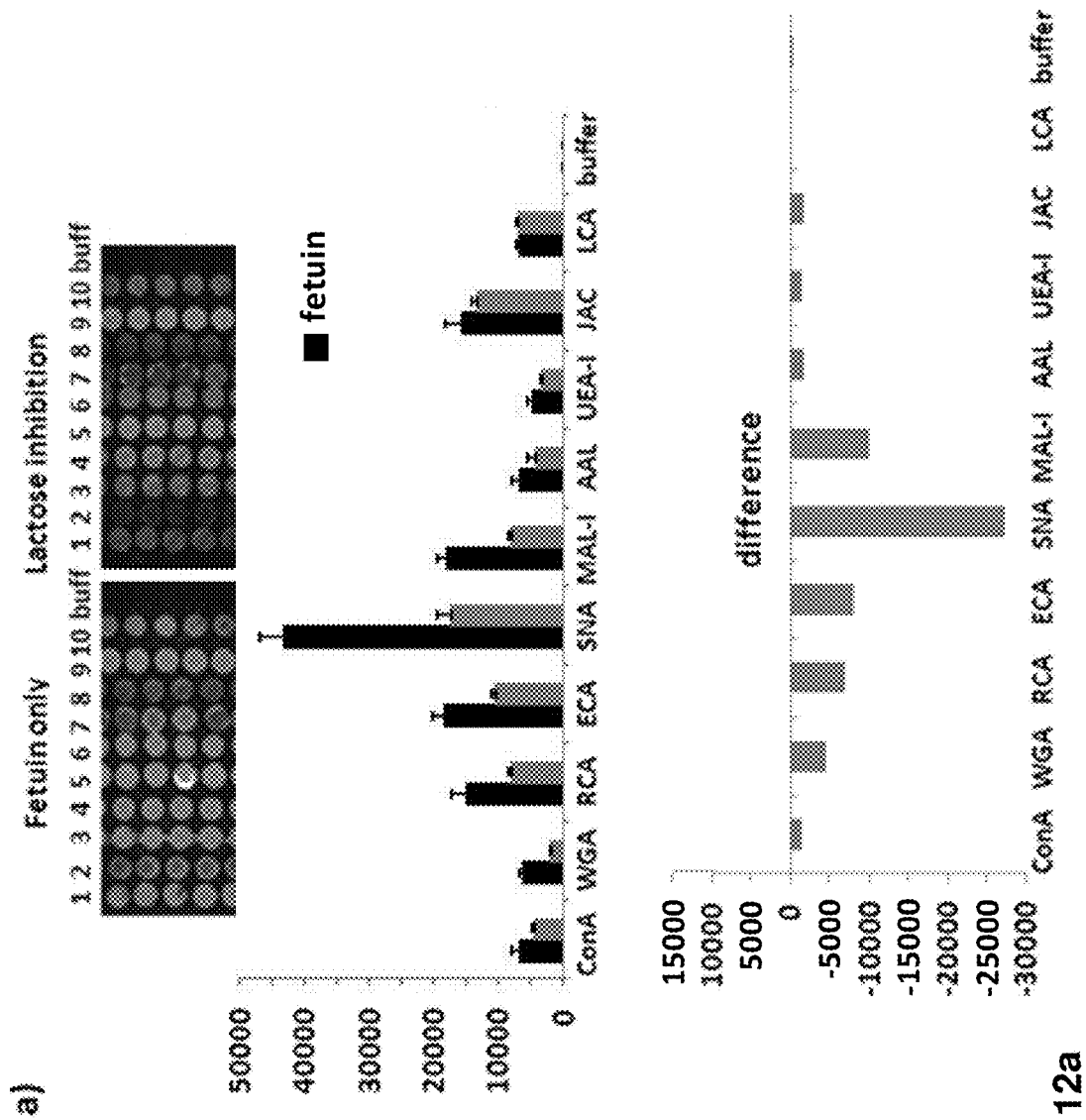
FIG. 12. a) Validation of the method with the analysis of the glycoprotein fetuin interaction with a slide containing 10 lectins. Inhibition with the monosaccharide lactose revealed the selectivity of the glycan-lectin interaction. b) Linearity of the fetuin-lectin interaction in a range of fetuin concentrations (4-800 ng).

A histogram view of lectin binding after electrophoresis and diffusion blotting of fetuin is given in FIG. 12. The binding pattern reflects well the reported presence of complex bi and triantennary oligosaccharides (ECA, RCA, ConA) and typical O-glycan chains (JAC), AAL binding indicates core and/or Lewis type fucosylation.

Figure 12B:
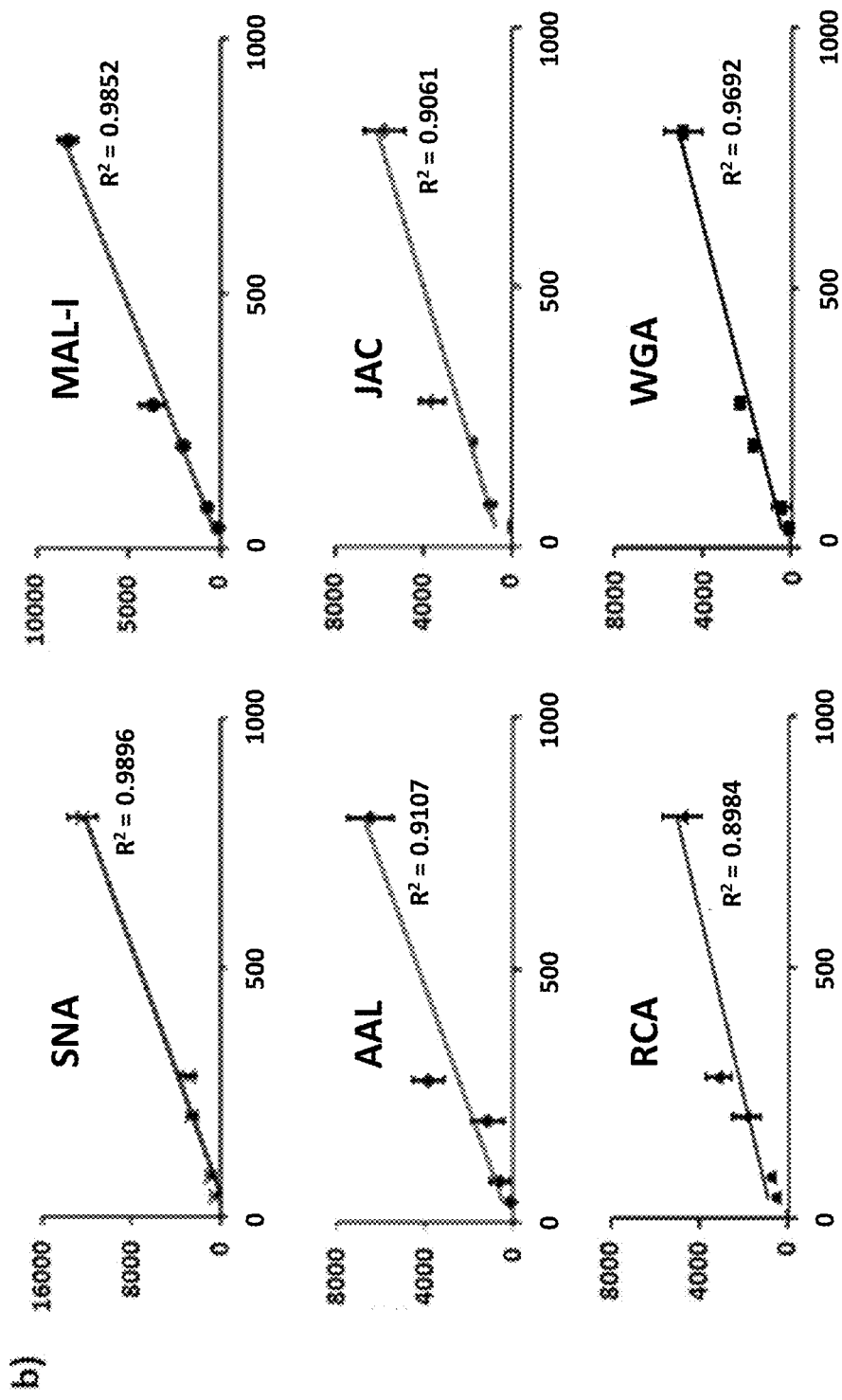

When lactose, which is known to inhibit RCA, ECA, SNA and MAL-1, was added to the transfer buffer the interaction of these lectins with fetuin was notable reduced (FIG. 12a), demonstrating the selectivity of the glycan lectin interaction. Fetuin was then run at 5 different concentrations (4, 80, 100, 300 and 800 ng of protein loaded) on the gel to study the linearity of the blotting for all 10 lectins. FIG. 12b shows a good linear response for the lectin binding to fetuin glycans for all 10 lectins over the entire concentration range from 4 to 800 ng of fetuin loaded onto the gel.

Figure 13:
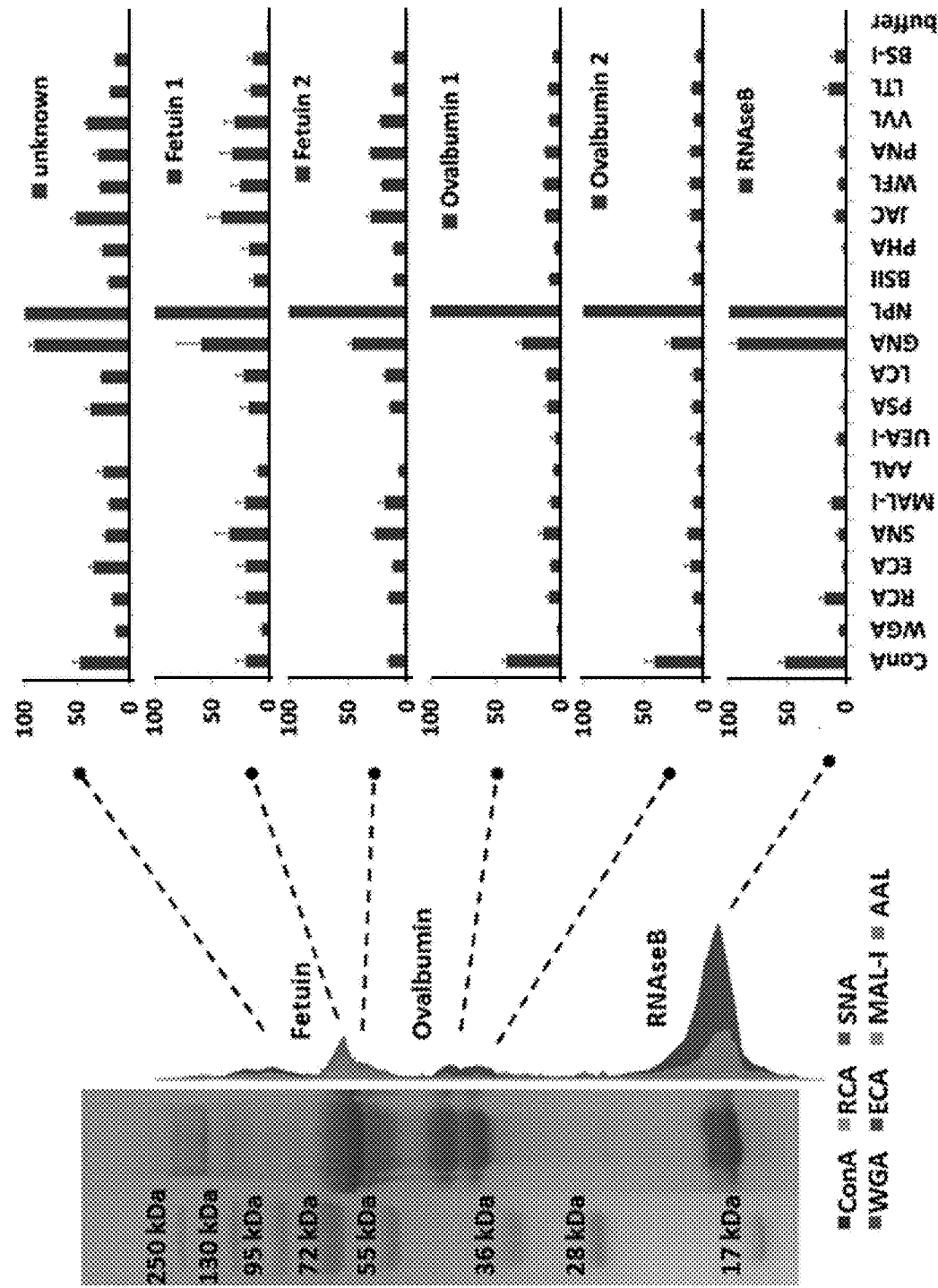
FIG. 13. Analysis of a synthetic mixture of glycoproteins: fetuin, ovalbumin, RNAseB and the non-glycosylated protein BSA. The mixture was fractionated by SDS-PAGE and transfer to a slide printed with 20 lectins. 6 different protein forms were detected and their glycosylation pattern shown in histograms.

Next the performance of the method for the simultaneous glycan analysis of various proteins in an artificial mixture was investigated (FIG. 13). Glyco proteins RNAse B, fetuin, ovalbumine and un-glycosylated BSA were chosen for their difference in masses and their well documented glycosylation patterns. In addition, the number of lectins included in the arrays was raised to 20 to enable a more differentiated analysis of protein glycosylation. To the ten previously employed lectins, *Galanthus nivalis* agglutinin (GNA) and *Narcissus pseudonarcissus* lectin (NPL), two mannose binding lectins, *Pisum sativum* (PSA) and *Lotus tetragonolobus* (LTL), which are specific for fucose, *Griffonia simplicifolia* (BS-II), a terminal GlcNAc binding lectin, *Phaseolus vulgaris* (PHA-E/L a mixture of lectins specific for complex oligosaccharides, *Wisteria floribunda* agglutinin (WFL), Peanut agglutinin (PNA), *Vicia villosa* lectin (VVL-B4) and *Griffonia simplicifolia* (BS-I), 4 lectins recognizing GalNAc and O-glycan epitopes were added. Lectins and buffer were printed in 1×21 arrays as previously explained maintaining the high resolution in the direction of electrophoretic separation.

The protein mixture was separated into 6 different bands by gel electrophoresis and diffusion-blotted to the 20-lectin array slide, while unglycosylated BSA was not transferred to the lectin array as expected. For RNAse B major interactions were observed only with mannose binding lectins ConA, GNA and NPL. Ovalbumin, a 45 kDa glycoprotein with a single glycosylation site occupied with high-mannose and to some degree with non-galactosylated hybrid N-glycans[27] was separated into two isoforms and the glycosylation analysed separately for both forms. No notable differences were found in the lectin interaction with both ovalbumin bands, with mannose recognizing lectins ConA, GNA and NPL as the major binding partners. Fetuin which had been with 10 lectins in a previous experiment was separated into two bands both showing a similar interaction profile with the 20 lectins. Differences in intensity of both profiles can be attributed to distinct concentration of the two isoforms. Interaction of moderate to strong intensities was observed for nearly all lectins reflecting the heterogenous glycosylation of fetuin with 3 N- and 3 O-glycosylation sites. A further band of an unknown protein impurity contained in the mixture was analyzed and showed a similarly strong interaction with the panel of lectins as fetuin but with a more pronounced binding to mannose binding lectins GNA and Con A.

Figure 14:
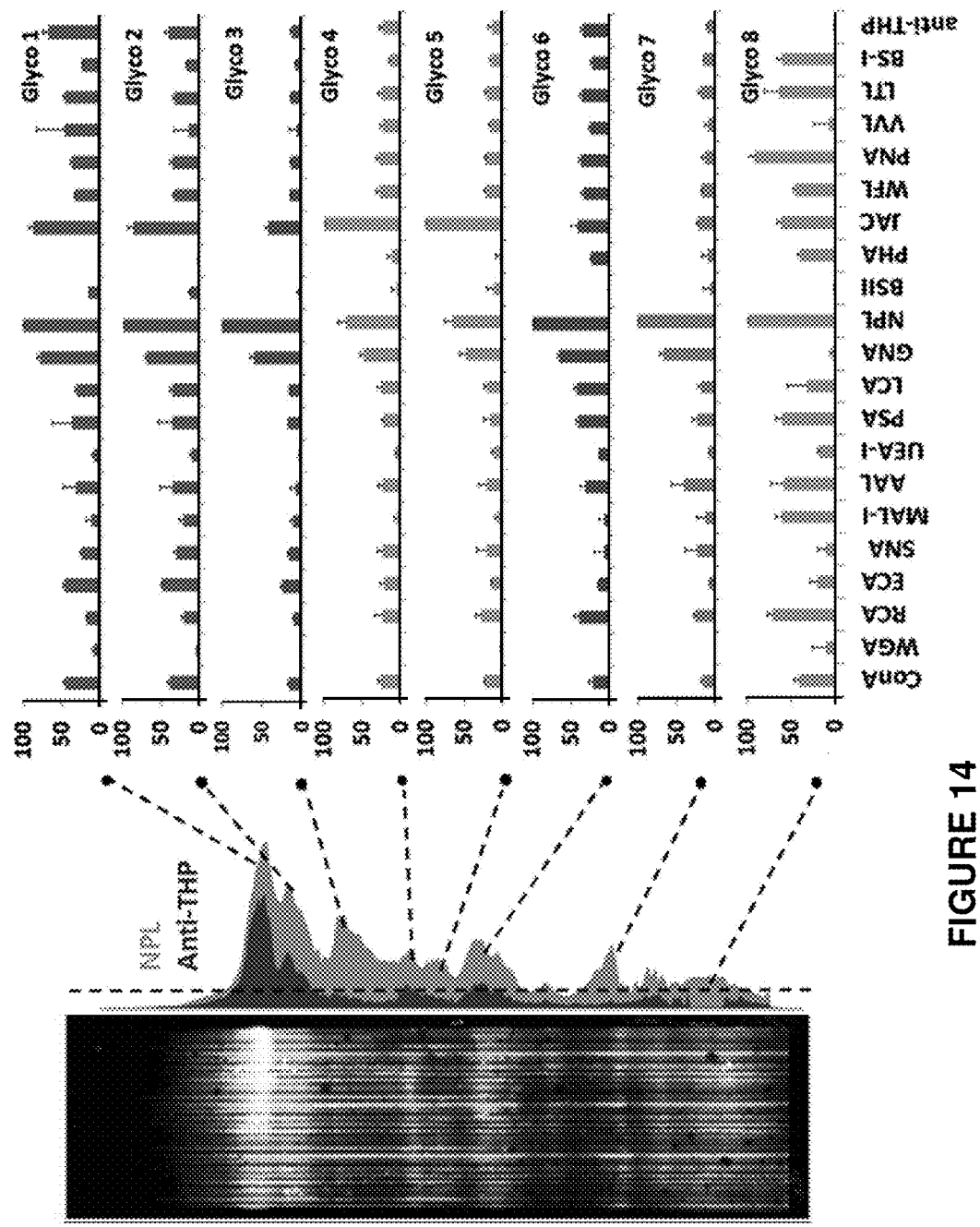
FIG. 14. Application of the method to the analysis of the glycosylation of urinary proteins. The figure shows the fluorescence image corresponding to the interaction of the urinary glycoproteins with a lectin array containing 20 lectins and an antibody to uromodulin.

The utility of the method herein disclosed was next tested in the analysis of the glycosylation pattern of urinary proteins. Urine is an often preferred biofluid in clinical diagnostics as it is very easy obtained in quantities sufficient for a broad range of analyses. High protein concentrations in urine are usually a sign of disease, so a sample from a healthy volunteer was concentrated via spin column prior to SDS-PAGE electrophoresis and the protein tagged with Cyanine-5. FIG. 14 shows the fluorescence image of the slide after the blot and its analysis in terms of the interaction with 20 lectins and with an antibody to uromodulin which was also included as the 21st probe. A major band at 70 kDa was identified as uromodulin by the antibody and other 6 bands were selected from the topographical image showing the carbohydrate lectin interaction for the entire gel and their binding pattern to the 20 lectin array. Large differences in the glycosylation of individual proteins are immediately visible and would go unnoticed on a traditional lectin array.

The invention claimed is:

1. A method for determining presence in a population of molecules of at least one first member of a binding pair having the capacity to bind specifically to at least one second member of said binding pair, the method comprising:
   (i) fractionating the population of molecules in a first support based on at least one physicochemical property of said at least one first member of the binding pair,
   (ii) transferring the fractionated molecules from said first support to a second support, wherein said second support is selected from the group consisting of a membrane, a silicone support, a glass support, a quartz support, a polyimide support, an acrylate support, a polymethylmethacrylate support, a ceramic support, a nitrocellulose support, a metal support, an amorphous silicon carbide support, and a polystyrene support that is uniformly coated by a set of microarrays, wherein each microarray of the set of microarrays comprises a plurality of second members of the binding pair with different affinities for the at least one first member of the binding pair and wherein said second members of the binding pair are immobilized in said second support, wherein said transferring of fractionated molecules is carried out under conditions suitable for maintaining in the second support a two-dimensional organization of the molecules fractionated in the first support and for allowing interaction between molecules of the population of molecules and the at least one second member of the binding pair coinciding spatially in the second support with said molecules, and
   (iii) detecting presence of molecules of the population of molecules in association with at least one second member of the binding pair,
   wherein the presence of molecules of the population of molecules associated with at least one second member of said binding pair in at least one microarray of the set of microarrays is indicative of the presence in the population of molecules of a first member of the binding pair with the capacity to bind specifically to said second member of the binding pair having physicochemical properties corresponding to a position in the first support coinciding spatially with one or more microarrays in which said first member of the binding pair is detected, and further wherein a first member of the at least one first member of the binding pair, the presence of which is to be determined in the population of molecules, is a glycoprotein, and the second member of the binding pair with the capacity to bind specifically to said first member of the binding pair is a lectin.

2. The method according to claim 1, wherein the molecules are fractionated by means of gel electrophoresis.

3. The method according to claim 2, wherein the gel electrophoresis is selected from the group of one-dimensional or two-dimensional gel electrophoresis.

4. The method according to claim 1, wherein the transfer of the fractionated molecules from the first support to the second support comprises an electrophoretic transfer or a diffusion transfer.

5. The method according to claim 1, wherein molecules of the population of molecules have been covalently modified with a tag before the fractionation.

6. The method according to claim 5, wherein the tag comprises a fluorescent group.

7. The method according to claim 5, wherein the method further comprises contacting the fractionated molecules present on the second support with a conjugate that comprises a molecule that binds to the tag and a detectable compound under conditions sufficient to form a complex comprising the conjugate and the tag, and detecting the complex.

8. The method according to claim 7, wherein the tag is biotin and the molecule that binds to the tag is neutravidin or a functionally equivalent variant thereof.

9. The method according to claim 7, wherein the detectable compound is fluorescently labeled or radioactively labeled.

\* \* \* \* \*